United States Patent
Ohodnicki, Jr. et al.

(10) Patent No.: US 9,019,502 B1
(45) Date of Patent: *Apr. 28, 2015

(54) ELECTRONICALLY CONDUCTIVE PEROVSKITE-BASED OXIDE NANOPARTICLES AND FILMS FOR OPTICAL SENSING APPLICATIONS

(71) Applicant: U.S. Department of Energy, Washington, DC (US)

(72) Inventors: Paul R. Ohodnicki, Jr., Alison Park, PA (US); Andrew M. Schultz, Pittsburgh, PA (US)

(73) Assignee: U.S. Department of Energy, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/335,149

(22) Filed: Jul. 18, 2014

Related U.S. Application Data

(63) Continuation of application No. 14/135,691, filed on Dec. 20, 2013, now Pat. No. 8,836,945.

(51) Int. Cl.
*G01N 21/00* (2006.01)
*G01N 21/55* (2014.01)
*G01N 21/78* (2006.01)

(52) U.S. Cl.
CPC ...... *G01N 21/783* (2013.01); *G01N 2201/0826* (2013.01)

(58) Field of Classification Search
USPC ............... 356/432–448, 246; 250/434, 548.1; 428/693, 471, 699, 446, 700, 701
See application file for complete search history.

(56) References Cited

U.S. PATENT DOCUMENTS 6,136,457 A * 10/2000 Miyano et al. ............. 428/820.4
6,258,459 B1 * 7/2001 Noguchi et al. ............. 428/446

(Continued)

OTHER PUBLICATIONS

Ando, "Recent advances in optochemical sensors for the detection of H2, O2, O3, CO, CO2 and H2O in air," Trends in Analytical Chemistry 25(10) (2006).

(Continued)

*Primary Examiner* — Sang Nguyen
(74) *Attorney, Agent, or Firm* — James B. Potts; Brian J. Lally; John T. Lucas

(57) ABSTRACT

The disclosure relates to a method of detecting a change in a chemical composition by contacting a electronically conducting perovskite-based metal oxide material with a monitored stream, illuminating the electronically conducting perovskite-based metal oxide with incident light, collecting exiting light, monitoring an optical signal based on a comparison of the incident light and the exiting light, and detecting a shift in the optical signal. The electronically conducting perovskite-based metal oxide has a perovskite-based crystal structure and an electronic conductivity of at least $10^{-1}$ S/cm, where parameters are specified at the gas stream temperature. The electronically conducting perovskite-based metal oxide has an empirical formula $A_xB_yO_{3-\delta}$, where A is at least a first element at the A-site, B is at least a second element at the B-site, and where $0.8 < x < 1.2$, $0.8 < y < 1.2$. Exemplary electronically conducting perovskite-based oxides include but are not limited to $La_{1-x}Sr_xCoO_3$, $La_{1-x}Sr_xMnO_3$, $LaCrO_3$, $LaNiO_3$, $La_{1-x}Sr_xMn_{1-y}Cr_yO_3$, $SrFeO_3$, $SrVO_3$, La-doped $SrTiO_3$, Nb-doped $SrTiO_3$, and $SrTiO_{3-\delta}$.

20 Claims, 15 Drawing Sheets

(56) References Cited

U.S. PATENT DOCUMENTS 6,555,256 B1 * 4/2003 Christen et al. .............. 428/697
2006/0131182 A1 * 6/2006 Mazanec et al. .............. 205/551

OTHER PUBLICATIONS

Korotcenkov, "Metal oxides for solid-state gas sensors: What determines our choice?," Materials Science and Engineering B 139 (2007).

Schleunitz et al., "Optical gas sensitivity of a metal oxide multilayer system with gold-nano-clusters," Sensors and Actuators B 127 (2007).

Gaspera et al., "CO optical sensing properties of nanocrystalline ZnO—Au films: Effect of doping with transition metal ions," Sensors and Actuators B 161 (2012).

Gaspera et al., "Enhanced optical and electrical gas sensing response of sol-gel based NiO—Au and ZnO—Au nanostructured thin films," Sensors and Actuators B 164 (2012).

Ando et al., "Combined effects of small gold particles on the optical gas sensing by transition metal oxide films," Catalysis Today 36 (1997).

Remmel et al., "Investigation on nanocrystalline copper-doped zirconia thin films for optical sensing of carbon monoxide at high temperature," Sensors and Actuators B 160 (2011).

Ohodnicki et al., "Plasmonic Transparent Conducting Metal Oxide Nanoparticles and Nanoparticle Films for Optical Sensing Applications," Thin Solid Films (2013), doi: 10.1016/j.tsf2013.04.145.

Cimitan et al., "Solvothermal synthesis and properties control of doped ZnO nanoparticles," Journal of Colloid and Interface Science 329 (2009).

Renganathan et al., "Gas sensing properties of a clad modified fiber optic sensor with Ce, Li and Al doped nanocrystalline zinc oxides," Sensors and Actuators B 156 (2011).

Tang et al., "Acidic ZSM-5 zeolite-coated long period fiber grating for optical sensing of ammonia," J. Mater. Chem. 21 (2011).

Jiang et al., "Multilayer fiber optic sensors for in situ gas monitoring in harsh environments," Sensors and Actuators B 177 (2013).

Wei et al, "Terbium doped strontium cerate enabled long period fiber gratings for high temperature sensing of hydrogen," Sensors and Actuators B 152 (2011).

Tang et al., "Proton-Conducting Nanocrystalline Ceramics for High-Temperature Hydrogen Sensing", Metallurgical and Materials Transactions E 48 (2014).

Apgar et al. "Enhanced Photoelectrochemical Activity in All-Oxide Heterojunction Devices based on Correlated "Metallic" Oxides," Advanced Materials 25 (2013).

Pellegrino et al. "Doping of $SrTiO_3$ thin films studied by spectroscopic ellipsometry", J. Phys. IV France 11 (2001).

Petrov et al. "Oxygen Nonstoichiometry of $La1-xSrxCoO3-d$ ($0<x<0.6$)" Journal of Solid State Chemistry 87 (1990).

* cited by examiner

ELECTRONICALLY CONDUCTIVE PEROVSKITE-BASED OXIDE NANOPARTICLES AND FILMS FOR OPTICAL SENSING APPLICATIONS

GOVERNMENT INTERESTS

The United States Government has rights in this invention pursuant to the employer-employee relationship of the Government to the inventors as U.S. Department of Energy employees and site-support contractors at the National Energy Technology Laboratory.

RELATION TO OTHER APPLICATIONS

This patent application claims priority from nonprovisional patent application Ser. No. 14/135,691 now U.S. Pat. No. 8,836,945 filed Dec. 20, 2013, which is hereby incorporated by reference.

FIELD OF THE INVENTION

One or more embodiments relates to a method of detecting a change in a chemical composition by contacting an electronically conducting perovskite-based oxide material with a gas stream, illuminating the electronically conducting perovskite-based oxide material, and detecting a shift in the optical signal. The electronically conducting perovskite-based oxide has a perovskite based crystal structure and an electronic conductivity of at least $10^{-1}$ S/cm, specified at the temperature of the gas stream to be monitored.

BACKGROUND

Improved sensors are needed that can operate in harsh environments for the next generation of technologies for higher efficiency, lower emission fossil-fueled power plants including oxy-fuel combustion processes for carbon capture and sequestration and coal gasification to produce syngas which can be converted to electrical power using solid-oxide fuel cells or gas turbines. Improved harsh environment sensors and controls would also enable significant gains in energy efficiency for the existing fleet of coal-fired power plants and a number of major domestic manufacturing industries. In particular, chemical sensors capable of operating at elevated temperatures in highly reducing, oxidizing, and/or corrosive environments can be leveraged across a broad range of applications including coal gasification, combustion turbines, solid oxide fuel cells, and advanced boiler systems.

Optical sensors are of increasing interest for a wide range of embedded sensing applications due to a number of inherent advantages as compared to other sensor technologies including the ability to monitor several different optical properties of a selected sensing material (transmission, reflection, luminescence). While there is a large body of existing work on electrical responses of semiconducting materials for applications in chemi-resistive based gas sensing, corresponding optical responses are not as well understood thereby providing very limited guidance for their applications in optical-based gas sensing. Material systems with useful optical responses specifically tailored for the application of interest are therefore required.

Metal oxides such as $WO_3$ have been utilized as optical sensors for $H_2$ while other metal oxides such as NiO and $Co_3O_4$ have been explored for optical sensing of reducing gases such as CO. However, these materials suffer from limited temperature stability in highly reducing conditions and typical dynamic ranges of measured output signals based on absorbance or reflectance have limited their practical use in a gas sensing instrument. See e.g. Ando, "Recent advances in optochemical sensors for the detection of $H_2$, $O_2$, $O_3$, CO, $CO_2$ and $H_2O$ in air," *Trends in Analytical Chemistry* 25(10) (2006); see also Korotcenkov, "Metal oxides for solid-state gas sensors: What determines our choice?" *Materials Science and Engineering B* 139 (2007). Incorporation of noble metals such as gold nanoparticles into these metal oxides has generally been employed to enable responses that are suitable for practical gas sensing. See e.g., Schleunitz et al., "Optical gas sensitivity of a metal oxide multilayer system with gold-nano-clusters," *Sensors and Actuators B* 127 (2007); see also Gaspera et al., "CO optical sensing properties of nanocrystalline ZnO—Au films: Effect of doping with transition metal ions," *Sensors and Actuators B* 161 (2012); see also Gaspera et al., "Enhanced optical and electrical gas sensing response of sol-gel based NiO—Au and ZnO—Au nanostructured thin films," *Sensors and Actuators B* 164 (2012); and see Ando et al., "Combined effects of small gold particles on the optical gas sensing by transition metal oxide films," *Catalysis Today* 36 (1997). In other cases, metal oxides such as ZnO with various dopants have been utilized and absorbance changes have been noted for gases such as ammonia, methanol, and ethanol, however the mechanism has generally been attributed to the adsorption of oxygen molecules at the metal oxide surface and the dopant was utilized to enhance catalytic activity, and correspondingly measurement temperatures have been limited to below about 100° C. The time constants for the measured responses also tend to be prohibitively long such that they are not practical for a gas sensing device. See e.g., Renganathan et al., "Gas sensing properties of a clad modified fiber optic sensor with Ce, Li and Al doped nanocrystalline zinc oxides," *Sensors and Actuators B* 156 (2011). Dopants such as CuO have also been employed with metal oxides such as $ZrO_2$ in order to provide sensing through reversible red-ox reactions, however such approaches can suffer from instability under high temperature and/or high reducing agent concentrations. See e.g., Remmel et al., "Investigation on nanocrystalline copper-doped zirconia thin films for optical sensing of carbon monoxide at high temperature," *Sensors and Actuators B* 160 (2011).

Weak dynamic range of optical responses of high temperature stable metal oxides to changing gas atmospheres has generally required investigators to amplify the response by applying them to optical fibers with fiber bragg gratings. For example, low electronic conductivity perovskite based oxides such as terbium doped strontium cerate have been integrated with long period fiber gratings and have demonstrated useful and selective responses to $H_2$ at elevated temperatures. By periodically modifying the refractive index of the core of the optical fiber, the interaction with a sensing layer can be enhanced by orders of magnitude. See e.g. Tang et al., "Acidic ZSM-5 zeolite-coated long period fiber grating for optical sensing of ammonia," *J. Mater. Chem.* 21 (2011); see also Jiang et al., "Multilayer fiber optic sensors for in situ gas monitoring in harsh environments," *Sensors and Actuators B* 177 (2013); see also Wei et al, "Terbium doped strontium cerate enabled long period fiber gratings for high temperature sensing of hydrogen," *Sensors and Actuators B* 152 (2011); see also Remmel et al., "Investigation on nanocrystalline copper-doped zirconia thin films for optical sensing of carbon monoxide at high temperature," *Sensors and Actuators B* 160 (2011); see also Tang et al., "Proton-Conducting Nanocrystalline Ceramics for High-Temperature Hydrogen Sensing", *Metallurgical and Materials Transactions E* 48 (2014). However, fiber bragg gratings typically exhibit an inherent temperature instability above 500° C. regardless of the sensing layer employed and dramatically increase device cost and complexity.

It would be advantageous to utilize a method that employs a class of metal oxides with relatively large and gas-sensitive optical absorption across a broad wavelength spectrum to maximize compatibility with the broadest possible range of optical sensor devices. Two primary wavelength ranges of interest for designing optical sensor devices include the visible range (~400-700 nm) and the near-infrared telecommunications wavelength range (~1500-1600 nm) for which a broad array of optical components, sources, and devices are commercially available and relatively inexpensive. It would be further advantageous if the class of materials provided adequate optical signal response to changes in chemical compositions to mitigate the need for utilization of advanced sensor designs such as fiber bragg gratings or for incorporation of noble metals, such as gold, platinum, and silver. It would be particularly advantageous if the method of improvement remained effective or even further improved at higher temperatures, in order to avoid the low temperature limitations associated with alternate methodologies. It would be further advantageous if the increased response of the metal oxide material could be brought about by relatively well understood processes, such as optimizing material chemistry, doping, optimization of deposition techniques and conditions, and carefully selected elevated temperature pretreatments prior to deployment for chemical sensing applications. It would be further advantageous if the material response demonstrated reversibility under high temperature conditions of interest.

Presented here is a method of detecting changes in the chemical composition of a gaseous stream by utilizing the optical response of an electronically conducting perovskite-based oxide material. The unique optical properties of the perovskite-based oxides are well known to derive from their electronic band structure which is intimately linked to the underlying crystal structure. Perovskite-based oxide materials with relatively high electronic conductivity such as $La_{1-x}Sr_xCoO_3$, $La_{1-x}Sr_xMnO_3$, $LaCrO_3$, $LaNiO_3$, $La_{1-x}Sr_xMn_{1-y}Cr_yO_3$, $SrFeO_3$, $SrVO_3$, La-doped $SrTiO_3$, Nb-doped $SrTiO_3$, and $SrTiO_{3-\delta}$ have been observed to display a relatively large and broad-band optical absorption across the entire wavelength range from the ultraviolet to the near-infrared. Suitable optimization of high temperature stable electronically conducting perovskite-based oxides for elevated temperature gas sensing applications can be achieved through (1) composition modification, (2) doping, (3) synthesis technique and details, and (4) post-synthesis pretreatments at elevated temperatures among others. The surprisingly effective method utilized within this disclosure provides a means whereby electronically conducting perovskite-based metal oxides are employed to generate improved signals under gaseous atmospheres which experience varying concentrations of reducing and oxidizing agents. In contrast with electronically conductive perovskite-based oxides, the optical absorption of common semiconductor metal oxides employed in chemi-resistive sensing applications such as ZnO, $TiO_2$, and $SnO_2$ are typically limited to wavelengths below the so-called band-edge and are associated with interband electronic transitions that are not strongly sensitive to changes in ambient gas atmospheres thereby making them less advantageous for high temperature optical gas sensing applications despite a well-known and well-characterized response of the electrical resistivity of such conventional metal oxide systems.

These and other objects, aspects, and advantages of the present disclosure will become better understood with reference to the accompanying description and claims.

SUMMARY

The disclosure provides a method of detecting a change in a chemical composition of a gas stream through the generally described steps of: (i) placing an electronically conducting perovskite-based oxide material comprising a conducting perovskite-based oxide in the gas stream; (ii) contacting the electronically conducting perovskite-based oxide material with a monitored stream comprising some portion of the gas stream; (iii) illuminating the electronically conducting perovskite-based oxide material with incident light; (iv) collecting exiting light transmitted, reflected, scattered, or a combination thereof by the electronically conducting perovskite-based oxide material; (v) monitoring an optical signal based on a comparison of the incident light and the exiting light using optical spectroscopy, and (vi) detecting a shift in the optical signal, thereby detecting the change in the chemical composition.

The electronically conducting perovskite-based oxide has an empirical formula $A_aB_bO_c$ where A is at least a first element, B is at least a second element, and O is an oxygen anion, and where the electronically conducting perovskite-based oxide has a perovskite-based crystal structure and an electronic conductivity of at least $10^{-1}$ S/cm at the temperature of the gas stream to be sensed. Exemplary electronically conducting perovskite-based oxides include but are not limited to $La_{1-x}Sr_xCoO_3$, $La_{1-x}Sr_xMnO_3$, $LaCrO_3$, $LaNiO_3$, $La_{1-x}Sr_xMn_{1-y}Cr_yO_3$, $SrFeO_3$, $SrVO_3$, La-doped $SrTiO_3$, Nb-doped $SrTiO_3$, and $SrTiO_{3-\delta}$. In some embodiments, the electronically conducting perovskite-based oxide is a non-stoichiometric metal oxide such as $SrTiO_{3-\delta}$ in which a non-stoichiometry is imparted through the details of the synthesis procedure resulting in an enhanced electronic conductivity and associated optical absorption as compared to corresponding stoichiometric perovskite oxides such as $SrTiO_3$.

The optical response of the electronically conducting perovskite-based oxide materials results from the electronic charge carriers and defects that are also responsible for the relatively high electronic conductivity, and the resulting impact of changing gas atmospheres on the population of defects and electronic charge carriers as well as their mobility. These changes are postulated to be the predominant mechanism responsible for the change in measured optical absorption as a result of changing ambient gas atmospheres. This surprising discovery is utilized to provide a means whereby electronically conducting perovskite-based oxides having relatively high electronic conductivity can be employed to generate useful signals indicating alterations in a surrounding gas atmosphere, based on resulting shifts in the optical signal.

In certain embodiments, the monitored stream has a temperature of at least 200° C. In a further embodiment, the monitored stream has a temperature of at least 200° C., and the change in the chemical composition is indicated by an increase or decrease in a signal-averaged optical signal of at least 0.1%. The optical response of the electronically conducting perovskite-based oxide material is additionally demonstrated to be monotonic relative to the concentration of a reducing or oxidizing gas. In an embodiment, the electronically conducting perovskite-based oxide material is utilized in a method for monitoring the concentration of a chemical species.

The same effects that are thought to be responsible for modifications to the optical absorption of electronically conducting perovskite-based oxide materials will also impact the degree of light scattering by the material. Light scattering is well known to be related to the degree of surface or interface roughness in the case of fairly dense and continuous thin films and particle size in the case of nanoparticle based films. In addition, the amount of light scattering is dependent upon the wavelength of interrogation and the optical constants of the conducting oxide material. In particular, surface roughnesses of continuous films greater than approximately 5 nm, 10 nm, or 50 nm can cause a significant degree of light scattering in the UV, visible, and near-IR wavelength ranges with increasing surface roughnesses causing increased light scattering. Similarly, particle sizes of nanoparticle based films greater than approximately 10 nm, 20 nm, or 50 nm in diameter can also cause a significant degree of light scattering in the UV, visible, and near-IR wavelength ranges. In general, increasing surface roughnesses and particle sizes tend to cause increased light scattering at a given wavelength. In some cases, enhanced scattering can result in larger optical signal shifts and even change the sign of the shift over certain wavelength ranges.

In the case of the electronically conducting perovskite-based oxide materials discussed here, the electrical resistivity of the electronically conducting perovskite-based oxide material is generally believed to be strongly related to the corresponding optical properties. As such, the useful optical responses that can be obtained in this class of materials can enable sensors that allow for gas composition to be monitored through both electrical and optical interrogation methods. The method disclosed here employs optical interrogation methods but it should be understood that in some embodiments the electronic (e.g. resistivity) properties of the electronically conducting perovskite-based oxide may also be monitored simultaneously.

The novel process and principles of operation are further discussed in the following description.

DETAILED DESCRIPTION

Figure 1:
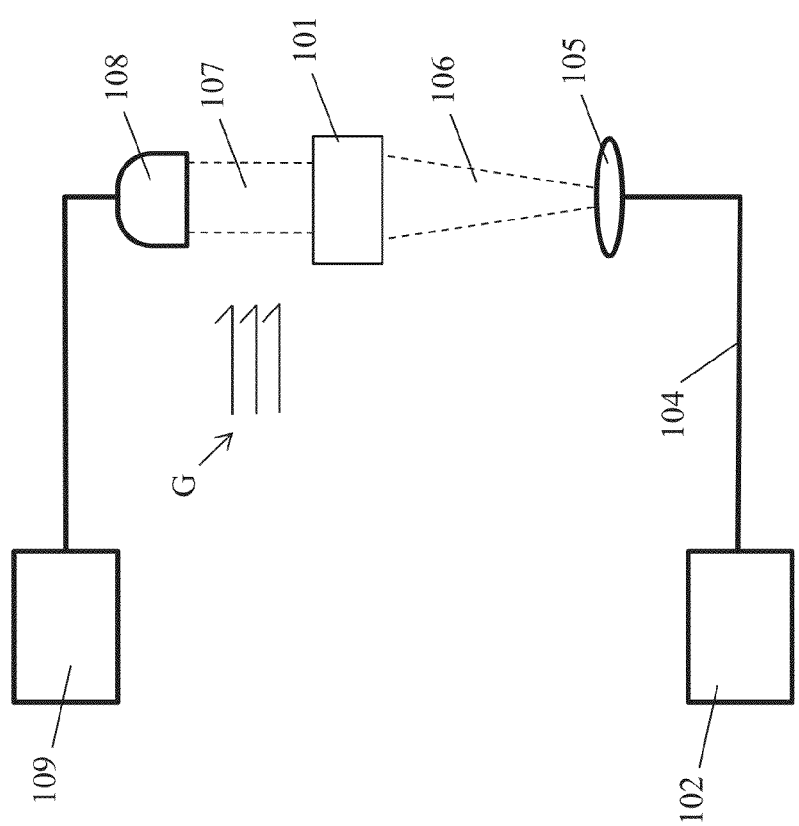
FIG. 1 illustrates a methodology for sensing changes to a chemical composition in a high temperature gas stream using the electronically conducting perovskite-based oxide material.

The following description is provided to enable any person skilled in the art to use the invention and sets forth the best mode contemplated by the inventor for carrying out the invention. Various modifications, however, will remain readily apparent to those skilled in the art, since the principles of the present invention are defined herein specifically to provide a method for detecting a change in the chemical composition of a gas stream using the optical response of an electronically conducting perovskite-based oxide material.

The disclosure provides a method for sensing changes to a chemical composition of a gas stream by utilizing a shift in the optical signal generated by an electronically conducting perovskite-based oxide material having a relatively high electronic conductivity. This disclosure utilizes the surprising impact of changes to the concentration and mobility of electronic charge carriers and defects that are also responsible for the relatively high electronic conductivity on the optical signals generated, and specifies a manner in which the optical signal of the electronically conducting perovskite-based oxide material may serve as an indication of changing gas atmospheres. The impact of alterations to these various parameters of a material on resulting optical signals generated within a gaseous atmosphere at relatively large levels is a surprising recognition. See U.S. patent application Ser. No. 14/135,691 filed Dec. 20, 2013 by Ohodnicki et al.; see also Ohodnicki et al., "Plasmonic Transparent Conducting Metal Oxide Nanoparticles and Nanoparticle Films for Optical Sensing Applications," *Thin Solid Films* (2013), doi: 10.1016/j.tsf.2013.04.145. In the case of the electronically conducting perovskite-based oxide materials disclosed here, the conductivity is generally believed to be strongly related to the corresponding optical properties through equivalent or similar phenomena. The origin of the observed optical absorption features in the electronically conducting perovskite-based oxides can be attributed to a number of different physical mechanisms which include: (1) excitation of itinerant free carriers, (2) hopping of localized electronic charge carriers or "polarons", (3) interband electronic transitions, (4) charge transfer reactions between cations or between cations and anions, and (5) electronic transitions associated with additional defect or impurity levels. See e.g. Apgar et al. "Enhanced Photoelectrochemical Activity in All-Oxide Heterojunction Devices based on Correlated "Metallic" Oxides," *Advanced Materials* 25 (2013); see also Pellegrino et al. "Doping of $SrTiO_3$ thin films studied by spectroscopic ellipsometry", *J. Phys. IV France* 11 (2001). In this class of materials, a number of parameters similar to those identified in aforementioned U.S. patent application Ser. No. 14/135, 691 are known to vary in response to changing atmospheric conditions at elevated temperatures. In $La_{1-x}Sr_xCoO_3$ systems for example, electronic conductivity was suggested to be associated with itinerant free electrons and the free electron concentration and the oxidation state of Co atoms were reported to vary with effective oxygen partial pressure. In corresponding $La_{1-x}Sr_xFeO_3$ systems, the electronic conductivity mechanism has been suggested to be associated with hopping-type conductivity of localized charge carriers and involves a change in oxidation state of Fe atoms which can also vary with effective oxygen partial pressure. See e.g. Petrov et al. "Oxygen Nonstoichiometry of $La_{1-x}Sr_xCoO_{3-d}$ ($0<x\leq0.6$)" *Journal of Solid State Chemistry* 87 (1990); see also Lankhorst et al., "Thermodynamic Quantities and Defect Structure of $La_{0.6}Sr_{0.4}Co_{1-y}Fe_yO_{3-d}$ (y=0-0.6) from High-Temperature Coulometric Titration Experiments", *Journal of Solid State Chemistry* 130 (1997).

This disclosure provides a method by which this surprising effect may be utilized in order to measurably detect alterations in a surrounding gas atmosphere, by utilizing electronically conductive perovskite-based oxide material with sufficiently high electronic conductivity such that the altered optical signal is measurably impacted. Due to the relatively large optical signal shifts that can be derived in this class of high electronic conductivity perovskite-based oxides, the need for advanced sensor devices is mitigated thereby avoiding their inherent limitations including temperature stability, cost, complexity, and others.

The basic principles of the method are illustrated at FIG. 1. At FIG. 1, light from light source 102 is directed along an optical fiber 104 and focused by lens 105 producing incident light 106 illuminating electronically conductive perovskite-based oxide material 101. Concurrently, exiting light 107 is collected behind the specimen using a probe 108 connected to a spectrophotometer 109. Data generated by spectrophotometer 109 or supporting equipment is processed, and an optical signal is displayed. The optical signal is a comparison of the incident light and the exiting light and indicates the absorption, transmission, reflection, and scattering of the incident light at certain wavelengths by electronically conductive perovskite-based oxide material 101. Electronically conductive perovskite-based oxide material 101 is additionally in contact with a gas stream G, where gas stream G is comprised of a chemical composition of gaseous constituents with concentrations that may vary over time. In an embodiment, gas stream G is periodically comprised of reducing species such as $H_2$, CO, $NH_3$, hydrocarbons, or mixtures thereof. As discussed, electronically conductive perovskite-based oxide material 101 comprises an electronically conductive perovskite-based oxide having a perovskite-based crystal structure and an electronic conductivity of at least $10^{-1}$ S/cm, at the gas stream temperature. In an embodiment, the electronically conductive perovskite-based oxide is a perovskite-based oxide such as $La_{1-x}Sr_xCoO_3$, $La_{1-x}Sr_xMnO_3$, $LaCrO_3$, $LaNiO_3$, $La_{1-x}Sr_xMn_{1-y}Cr_yO_3$, $SrFeO_3$, $SrVO_3$, La-doped $SrTiO_3$, Nb-doped $SrTiO_3$, $SrTiO_{3-\delta}$, and others. Incident light 106, exiting light 107, and electronically conductive perovskite-based oxide material 101 generate an optical signal which depends on the chemical composition of monitored stream G, and shifts in the optical signal at monitored wavelengths are indicative of a change in the chemical composition.

Figure 2:
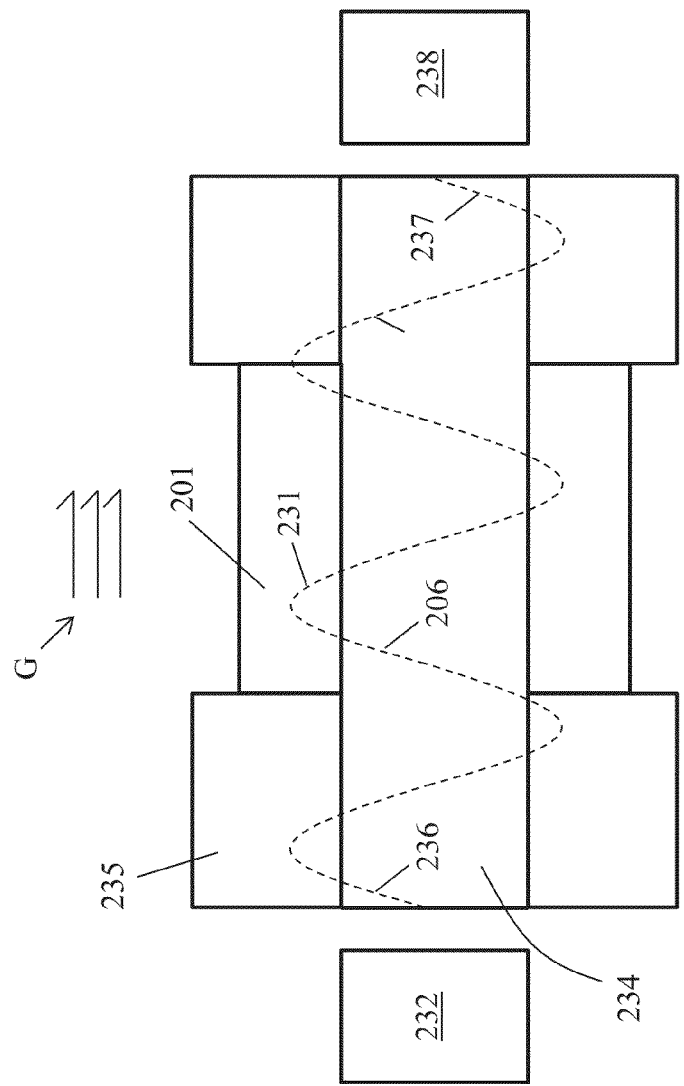
FIG. 2 illustrates electronically conducting perovskite-based oxide material configuration suitable for the detection of changes to a chemical composition using a waveguide sensor.

An additional embodiment of the method involves the interrogation of the electronically conductive perovskite-based oxide material by using an optical waveguide based device such as an optical fiber as illustrated at FIG. 2. An exemplary embodiment involves coating the core of an optical fiber with an electronically conductive perovskite-based oxide material that is in contact with the gas stream of interest. Interrogation light is launched into the waveguide based device, penetrates into the electronically conductive perovskite-based oxide material to probe the optical properties of the layer, and is eventually collected by a detector. In this embodiment, the conductive perovskite-based oxide material is illuminated by a wave propagating along a waveguide, such as a fiber optic cable. At FIG. 2, the waveguide is comprised of a core material 234 in contact with a cladding material 235, where core material 234 has a refractive index greater than cladding material 235. For example, core material 234 and cladding material 235 may be comprised of silica and various additions such as germanium, titanium, phosphorous, boron, fluorine, or other dopants in order to alter the respective refractive indices and meet the necessary criteria. At FIG. 2 light source 202 emits light into core material 234, generating wave 236 and penetrating cladding material 235, and conductive perovskite-based oxide material 201 having the properties disclosed is placed in contact with core material 234. Some portion of wave 236 provides incident light 206 such that conductive perovskite-based oxide material 201 is illuminated by evanescent wave 231 as illustrated. Conductive perovskite-based oxide material 201 is additionally in contact with monitored stream G comprised of gaseous constituents. Exiting light 207 is collected by probe 238. Interaction of conductive perovskite-based oxide material 201 with monitored stream G and illumination by incident light 206 enables detecting a change in the chemical composition of monitored stream G by detecting a shift in the optical signal, as earlier described. As is understood, the optical power and penetration depth of the evanescent wave into cladding material 235 and conductive perovskite-based oxide material 201 can be described by Beer-Lambert law. See e.g., Dickinson et al., "Convergent, Self-Encoded Bead Sensor Arrays in the design of an Artificial Nose," *Anal. Chem.* 71 (1999), among others. Additionally, the optical power coupled into the evanescent field may be improved by various methods such as bending, optimizing the relative refractive indices of the core and cladding, use of hollow fibers, and other methods. See e.g., Elosua et al., "Volatile Organic Compound Optical Fiber Sensors: A Review," *Sensors* 6 (2006), among others.

Generally, the magnitude of the optical signal response produced by the conductive perovskite-based oxide materials disclosed here allows configurations such as FIG. 2 without necessary recourse to mechanisms such as long-period fiber bragg gratings within core material 234, and the refractive index of core material 234 may be relatively homogenous in the region between incident light 206 and exiting light 207. In a particular embodiment, the homogeneity of core material 234 is such that the refractive index of core material 234 is within $+/-10^{-7}$ refractive index units of some constant value, where the constant value is expressed in refractive index units.

The electronically conducting perovskite-based oxide material comprises an electronically conducting perovskite-based oxide, where the electronically conducting perovskite-based oxide has an electronic conductivity of at least $10^{-1}$ S/cm, where the conductivity is measured at the gas stream temperature. The electronically conducting perovskite-based oxide exhibits a perovskite based crystal structure having an empirical formula $A_xB_yO_{3-\delta}$, where A is at least a first element at the A-site, B is at least a second element at the B-site, and O is an oxygen anion coordinated with both A and B. Additionally, $0.8<x<1.2$, $0.8<y<1.2$, and $\delta$ is a positive or negative number having an absolute value greater than or equal to zero. In some embodiments, $\delta$ has an absolute value less than 0.5, and in other embodiments less than 0.3, and in still other embodiments less than 0.1. Further, when A and B are present in stoichiometric proportion and $x=1$, $y=1$, and $\delta=0$, each A-site cation is coordinated to twelve oxygen anions and each B-site cation is coordinated to six oxygen anions. Such perovskite based crystal structures are known in the art. See e.g., Crystallography and Chemistry of Perovskites, M. Johnsson and P. Lemmens, in "Handbook of Magnetism and Advanced Magnetic Media", Ed. H. Kronmüller, John Wiley & Sons, New York, (2006), among others. The electronic conductivity of the electronically conducting perovskite-based oxide is preferably at least $10^0$ S/cm, more preferably at least $10^1$ S/cm, and most preferably at least $10^2$ S/cm. In the most preferred embodiments, the electronically conducting perovskite-based oxide thus has electronic conductivities comparable to or greater than the group of materials known generically as transparent conducting oxides.

Further, in an embodiment, A is at least a first element A' and a second element A" and the electronically conducting perovskite-based oxide has the empirical formula $A'_{(x-a)}A''_aB_yO_{3-\delta}$; where A' and A" occupy the A-site of the perovskite-based crystal structure. In a further embodiment, the electronically conducting perovskite-based oxide has the empirical formula $A_xB'_{(y-b)}B''_bO_{3-\delta}$, where B' and B" occupy the B-site of the perovskite-based crystal structure. In a further embodiment, the electronically conducting perovskite-based oxide has the empirical formula $A'_{(x-a)}A''_aB'_{(y-b)}B''_bO_{3-\delta}$, where A', A", B', and B" are as earlier defined. Exemplary electronically conducting perovskite-based oxides include but are not limited to $La_{1-x}Sr_xCoO_3$, $La_{1-x}Sr_xMnO_3$, $LaCrO_3$, $LaNiO_3$, $La_{1-x}Sr_xMn_{1-y}Cr_yO_3$, $SrFeO_3$, $SrVO_3$, La-doped $SrTiO_3$, Nb-doped $SrTiO_3$, and $SrTiO_{3-\delta}$. In an additional embodiment, the A', A", B', and B" are metals within groups 2-15. In another embodiment, the B' or B" element is the same element as A' or A", but with a different oxidation state. In another embodiment, the oxygen atom is partially substituted with another anion such as F or Cl. In a further embodiment, A" and B" comprise less than 15 weight percent (wt. %) of the electronically conducting perovskite-based oxide, such that within the $A'_{(x-a)}A''_aB'_{(y-b)}B''_bO_{3-\delta}$ formulation, $(a+b)/(x+y+3)<0.15$.

Figure 15:
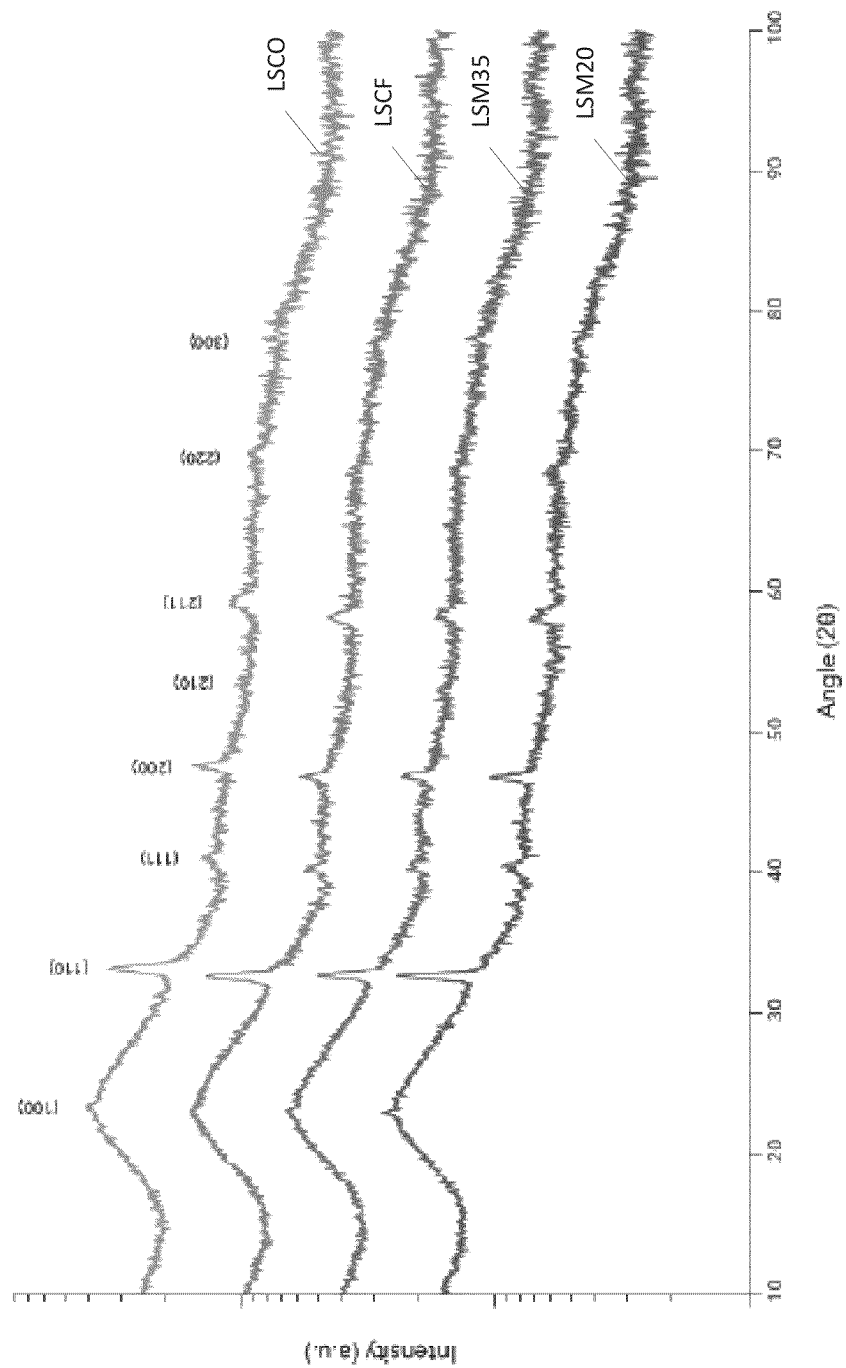
FIG. 15 illustrates an XRD identifying a perovskite structure.

Evidence of the perovskite-based crystal structure may be obtained using any means known in the art. For example, the perovskite-based crystal structures may be recognized through x-ray diffraction patterns, such as those at FIG. 15. FIG. 15 illustrates x-ray diffraction patterns for $La_{1-x}Sr_x$-$CoO_3$, $La_{1-x}Sr_xCo_{1-y}Fe_yO_3$, $La_{0.65}Sr_{0.35}MnO_3$, and $La_{0.80}Sr_{0.20}MnO_3$, designed as LSCO, LSCF, LSM35 and LSM20 respectively. In all cases, the observed peaks can be clearly indexed to the perovskite crystal structure.

Figure 3:
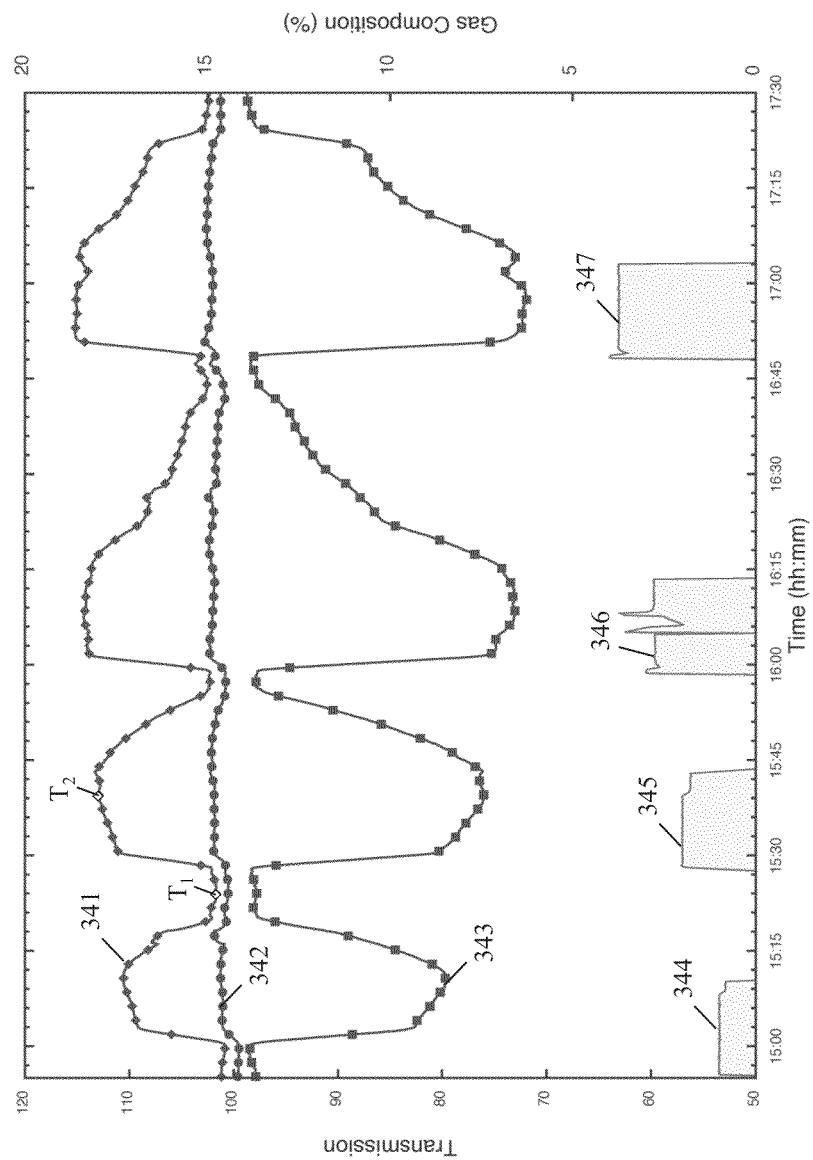
FIG. 3 illustrates a change in the optical transmission of an LSM electronically conducting perovskite-based oxide in response to changes to a chemical composition in the near-infrared wavelength range.

As an illustration of the methodology, FIG. 3 represents exemplary optical signals expected for an electronically conductive perovskite-based oxide material comprising $La_{0.8}Sr_{0.2}MnO_3$ when the $La_{0.8}Sr_{0.2}MnO_3$ electronically conductive perovskite-based oxide material is illuminated by incident light and exposed to a monitored stream at a gas stream temperature of approximately 700° C. As indicated, the particular optical signals at FIG. 3 represent the film transmission at several selected wavelengths, where 341 illustrates the optical signal at a wavelength of about 1800 nm, 342 illustrates the optical signal at a wavelength of about 2100 nm, and 343 illustrates the optical signal at a wavelength of about 2500 nm. The chemical composition of the monitored stream is $N_2$ with varying levels of $H_2$, where the % $H_2$ is illustrated at 344, 345, 346, and 347 and indicates % $H_2$ according to the Gas Composition (%) axis. When the chemical composition of the monitored stream varies, such that the monitored stream comprises a range from 1% $H_2$, remainder $N_2$, up to 4% $H_2$, remainder $N_2$, the optical signal is observed to exhibit a pronounced shift that depends upon the interrogation wavelength.—For example, as illustrated at FIG. 3, optical signal 341 produces a transmission $T_1$ generated when the monitored stream is $N_2$ with an absence of $H_2$, and illustrates a pronounced shift to a transmission $T_2$ when the monitored stream is altered to 2% $H_2$/background $N_2$. The shift in the optical signal at a single wavelength is observed to be monotonic with increasing levels of $H_2$ in a $N_2$ background over this range, and the recovery time is observed to be sufficiently short for practical application as a sensor material. Additionally, at the interrogation wavelength of about 1800 nm (optical signal 341), the optical signal is observed to shift in a positive direction with increasing $H_2$ by as much as 15%, while the corresponding signal shift for an interrogation wavelength of about 2500 nm (optical signal 343) is in the negative direction by more than 25%. These signal shifts are extremely large for a sensor material that is monitored in a transmission geometry which is one of the significant advantages of this class of electronically conductive perovskite-based oxide materials.

Figure 4:
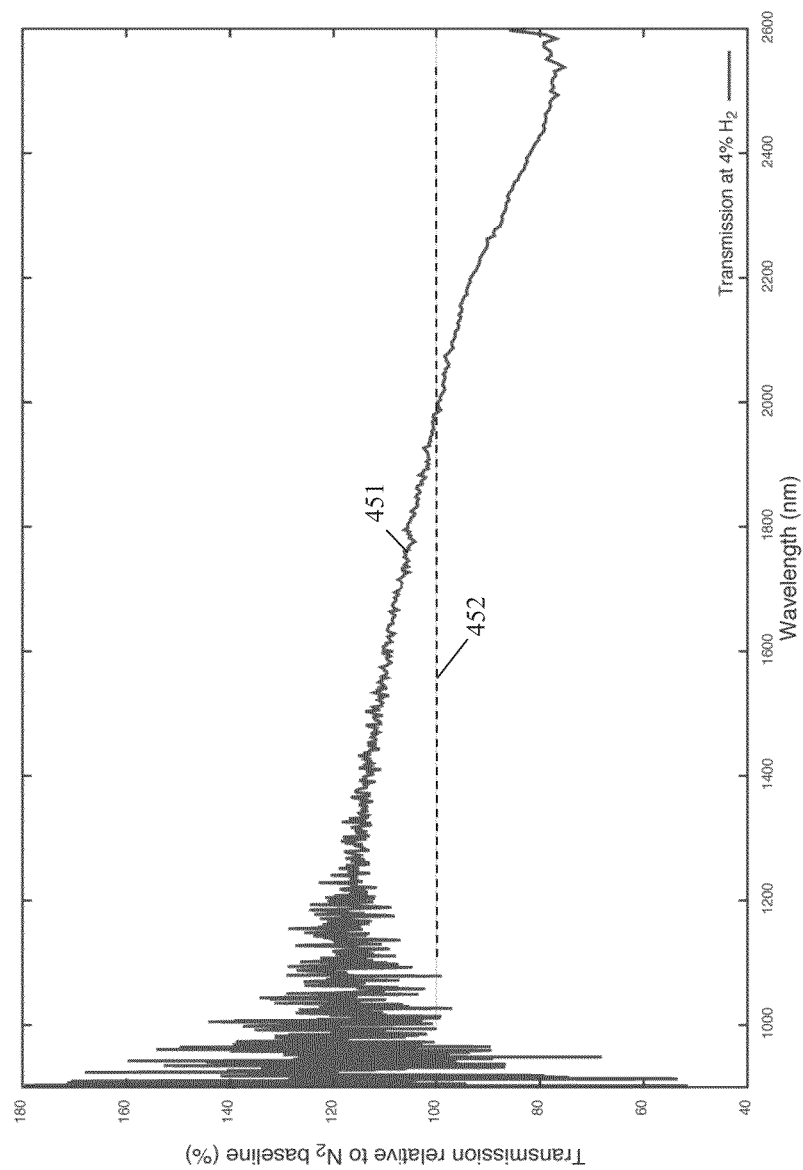
FIG. 4 illustrates the change in the optical transmission of the LSM electronically conducting perovskite-based oxide in response to changes to a chemical composition over a wide wavelength range.

Additionally, FIG. 4 illustrates an overall shift 451 in the optical signal for the $La_{0.8}Sr_{0.2}MnO_3$ when exposed to a gas stream comprised of 4% $H_2$, remainder $N_2$, relative to a $N_2$ baseline 452 over a wide wavelength range from about 1000 nm to about 2600 nm, and shows a particular subset of the wavelength range at which a reduced sensitivity is observed (between ~1900-2100 nm). Such wavelength dependent responses with wavelength regions of insensitivity are advantageous because they can be leveraged for use in multiple wavelength or broadband interrogation approaches to perform multi-parameter monitoring. For example, in some cases it has been demonstrated that information about both temperature and chemical composition of a gas stream can be derived by multi-wavelength or broadband wavelength optical interrogation of functional sensor materials. See e.g. Ohodnicki et al. "High Temperature Optical Sensing of Gas and Temperature Using Au-Nanoparticle Incorporated Oxides" *Sensors and Actuators B: Chemical* 202 (2014); see also Ohodnicki et al. "Plasmonic nanocomposite thin film enabled fiber optic sensors for simultaneous gas and temperature sensing at extreme temperatures" *Nanoscale* 5 (2013).

Figure 6:
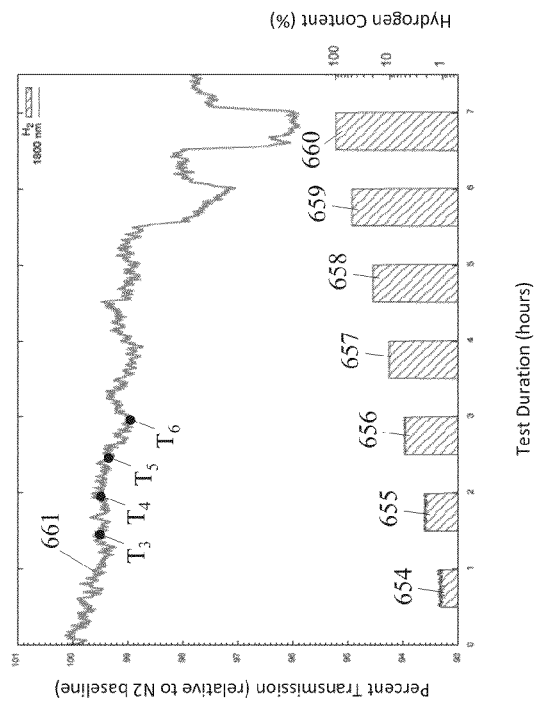
FIG. 6 illustrates a change in the optical transmission of the $SrTiO_3$ electronically conducting perovskite-based oxide in response to changes to a chemical composition.
Figure 5:
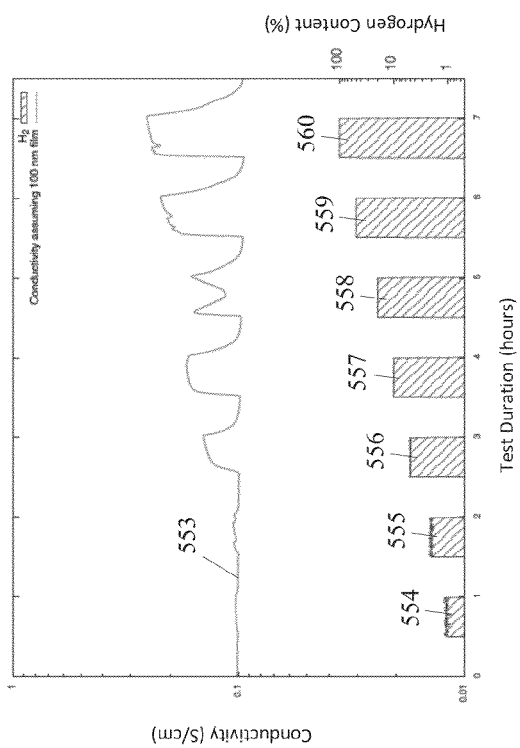
FIG. 5 illustrates increased electronic conductivity of an $SrTiO_3$ electronically conducting perovskite-based oxide in response to changes to a chemical composition.

The significance of the electrical conductivity of the electronically conductive perovskite-based oxides within this methodology may be illustrated with reference to FIGS. 5 and 6. FIG. 5 illustrates the conductivity 553 of an electronically conductive perovskite-based oxide material comprising $SrTiO_3$ in response to a monitored stream of $N_2$ with varying levels of $H_2$, where the % $H_2$ is illustrated at 554, 555, 556,

557, 558, 559, and 560 indicating % $H_2$ according to the Hydrogen Content (%) axis. As indicated, at exposures of about 2% $H_2$ and 4% $H_2$ with background $N_2$ (554 and 555 respectively), conductivity of the conductive perovskite-based oxide $SrTiO_3$ is generally around $10^{-1}$ S/cm, with the conductivity 553 increasing as the % H2 increases at 556, 557, 558, 559, and 560. The significance of the increasing conductivity is recognized by comparison with FIG. 6, which indicates an optical signal 661 as a change in transmission of the conductive perovskite-based oxide $SrTiO_3$ when illuminated at 1800 nm, and under the same varying levels of $H_2$, illustrated at 654, 655, 656, 657, 658, 659, and 660. As comparison of FIGS. 5 and 6 illustrates, increasing electrical conductivity levels have a significant impact on the shift in the optical signal 661 generated as a result of $H_2$ exposure. For exposures of about 2% $H_2$ and 4% $H_2$ with background $N_2$ (654 and 655 respectively, and corresponding to a conductivity generally around $10^{-1}$ S/cm), the electronically conductive perovskite-based oxide material comprising $SrTiO_3$ provides limited measurable response. In contrast, as the % $H_2$ increases at 656, 657, 658, 659, and 660 (and conductivity 553 correspondingly increases), the response significantly improves. For example, the impact of increasing conductivity is readily identified through comparison of the shift in the optical signal between $T_3$ and $T_4$, experienced at a conductivity generally around $10^{-1}$ S/cm, and comparison of the shift in the optical signal between $T_5$ and $T_6$, experienced at a conductivity which exceeds $10^{-1}$ S/cm. These results demonstrate that in addition to optical signal shifts, electrical signal shifts can also be monitored in this class of materials. The ability to perform both optical and electronic interrogation of the electronically conducting perovskite based oxides to monitor gas stream composition can potentially enable improved selectivity, sensitivity, or even multi-parameter sensing using a single sensor element with advanced sensor designs.

The methodology thus provides a method of detecting a change in a chemical composition of a gas stream through the generally described steps of: (i) contacting an electronically conducting perovskite based oxide material with a gas stream, where the electronically conducting perovskite based oxide material comprises a electronically conducting perovskite based oxide having an electronic conductivity of at least $10^{-1}$ S/cm at the gas stream temperature; (ii) illuminating the electronically conducting perovskite based oxide material with incident light; (iii) collecting exiting light transmitted, reflected, or a combination thereof by the electronically conducting perovskite based oxide material; (iv) monitoring an optical signal based on a comparison of the incident light and the exiting light using optical spectroscopy, and (v) detecting a shift in the optical signal, thereby detecting the change in the chemical composition.

Here, "optical signal" means a comparison of light incident on the electronically conducting perovskite based oxide material and light exiting the electronically conducting perovskite based oxide material at one or more wavelengths using optical spectroscopy. The optical signal may be expressed as, for example, a transmittance at the one or more wavelengths, an absorption at the one or more wavelengths, or any other parameters which indicate the absorption, transmission, reflection, or scattering impacts on the incident light as a result of interaction with the electronically conducting perovskite based oxide material. As is understood, optical spectroscopy based on a comparison of the incident light and the exiting light may indicate the absorption, transmission, reflection, or scattering which occur as a result of interaction between the incident light and the electronically conducting perovskite based oxide material. See e.g., Ingle, James D., and Stanley R. Crouch, *Spectrochemical analysis*, Englewood Cliffs, N.J.: Prentice Hall, 1988; see also Sole, Jose, *An Introduction to the Optical Spectroscopy of Inorganic Solids* (2005); see also Sarid, Dror and Challener, William, *Modern Introduction to Surface Plasmons: Theory, Mathematica Modeling, and Applications* (2010), among others.

Additionally, a "shift in the optical signal" means a variation between a first optical signal and a second optical signal at one or more wavelengths, where the first optical signal is generated at a first time and the second optical signal is generated at a second time, and where both the first optical signal and the second optical signal are generated by illuminating the electronically conducting perovskite-based oxide material with the light source emitting the incident light, collecting the exiting light, and comparing the incident light and the exiting light using optical spectroscopy. The shift in the optical signal may be recognized by detecting a variation between optical signals at any monitored wavelength or by variations at multiple wavelengths over a band of wavelengths. For example, the variation may be detected by monitoring a transmittance at a specific wavelength, the specific wavelength of an optical signal edge within a specified wave length range, the wavelength of an optical signal local maxima, a variation in the optical signal breadth, a variation in the optical signal amplitude, a variation in the optical signal full width at half maximum (FWHM), or any other techniques which may serve to indicate a variation between the first optical signal and a second optical signal. In an embodiment, the shift in the optical signal means a variation of at least 0.1% between a first time-averaged optical signal and a second time-averaged optical signal in either transmittance, absorption, or reflectance at a specific wavelength.

The shift in the optical signal as disclosed here is generally not constrained to a specific wavelength or band of wavelengths. As discussed, the shift in optical signal may be a shift at one specific wavelength, or may be a shift over a monitored band of wavelengths. For example, the shift may occur at one or more wavelengths typically considered to be ultraviolet, visible, or infrared as those terms are used in the art.

Figure 7:
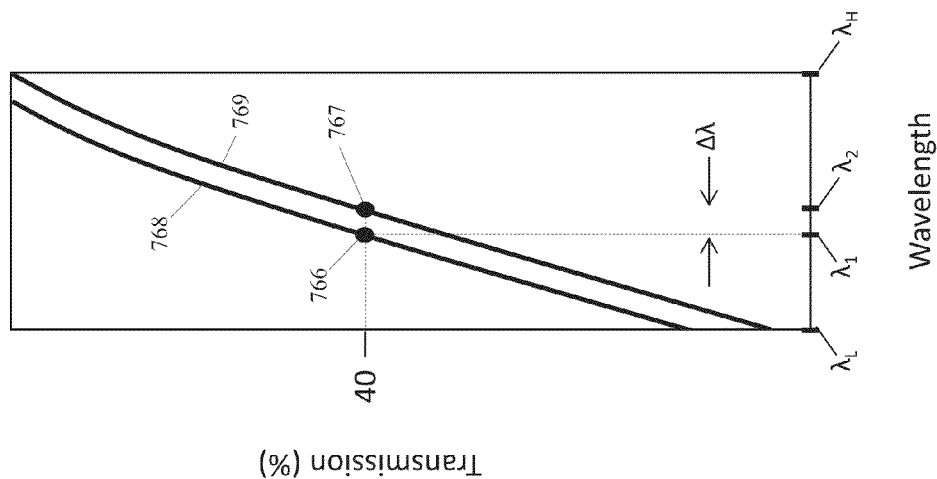
FIG. 7 illustrates a shift in an optical signal edge in response to changes to a chemical composition.

Additionally within this disclosure, the optical signal may be described as an optical signal edge. An "optical signal edge" when specified as present within a described wave length range means a specific wavelength where a specified percentage of the incident light is transmitted, absorbed, reflected, or scattered through the temperature sensing material. For example, at FIG. 7, points 726 and 727 on traces 728 and 729 respectively, indicating a transmission percentage of about 40% on the respective traces within a wavelength range from a $\lambda_L$ to $\lambda_H$. Similarly, a "shift in the optical signal edge" means a wavelength difference between a first wavelength and a second wavelength, where the specified percentage of the incident light is transmitted, absorbed, reflected, or scattered through the temperature sensing material at both the first wavelength and the second wavelength. For example, at FIG. 7, a shift in the optical signal edge $\Delta\lambda$ which occurs at the specified percentage of about 40% at FIG. 7 between the first wavelength $\lambda_1$ and the second wavelength $\lambda_2$.

As discussed, the method disclosed is based in part on the recognition that alterations to the concentration and mobility of electronic charge carriers and defects that are also responsible for the relatively high electronic conductivity of a material also impact the resulting optical signals generated, and that electronically conducting perovskite-based oxides are particularly effective for the measurable detection of alterations in a surrounding gas atmosphere. Correspondingly, electronically conducting perovskite-based oxides suitable for the method disclosed are described in terms of the perovskite-based crystal structure and the physical parameters possessed by the electronically conducting perovskite-based oxide, such as an electronic conductivity of at least $10^{-1}$ S/cm. As is understood in the art, for a given metal oxide, these physical parameters may be manipulated by various physical processes, such as annealing treatments, certain manners of deposition, and other means. These parameters may also vary with the composition of the gas stream to be sensed at a fixed temperature. See e.g Pellegrino et al. "Doping of $SrTiO_3$ thin films studied by spectroscopic ellipsometry", *J. Phys. IV France* 11 (2001); see also Chen et al., "Influence of Hydrogen on Al-doped ZnO Thin Films in the Process of Deposition and Annealing," *Transactions of Electrical and Electronic Materials* 10(3) (2009); see also Ota et al., "Fabrication of indium-tin-oxide films by dip coating process using ethanol solution of chlorides and surfactants," *Thin Solid Films* 411 (2002); see also Shigeno et al., "Formation of indium-tin-oxide films by dip coating process using indium dipropionate monohydroxide," *Thin Solid Films* 411 (2002), among others. Correspondingly, when this disclosure describes an electronically conducting perovskite-based oxide, where the electronically conducting perovskite-based oxide exhibits a perovskite-based crystal structure and has an electronic conductivity of at least $10^{-1}$ S/cm at the gas stream temperature, this is not intended to limit the electronically conducting perovskite-based oxide to those materials which display those parameters under all conditions and following all treatments. Rather, the method disclosed herein is intended to apply specifically when an electronically conducting perovskite-based oxide meets those conditions, regardless of whether those parameters can be manipulated by other processes existing outside this disclosure.

In some embodiments, the electronically conducting perovskite-based oxide is a non-stoichiometric electronically conducting perovskite-based oxide having an electronic conductivity of at least $10^{-1}$ S/cm and a perovskite-based crystal structure, where parameters are specified at the gas stream temperature. The electronic carrier concentration of the electronically conducting perovskite-based oxide is preferably at least $10^{17}/cm^3$, more preferably at least $10^{18}/cm^3$, and most preferably at least $10^{19}/cm^3$ The electronic conductivity is preferably at least $10^0$ S/cm, more preferably at least $10^1$ S/cm, even more preferably at least $10^2$ S/cm, and most preferably at least $10^3$ S/cm. The non-stoichiometric oxide may be, for example, of anion vacancy type, cation vacancy type, anion interstitial type, or cation interstitial type, as those terms are used in the art. See e.g., R. Xu et al., *Modern Inorganic Synthetic Chemistry* (2011), among others. Here, "non-stoichiometric oxide" means a electronically conducting perovskite-based oxide having the elemental composition $A_xB_yO_{3-\delta}$ where A is at least a first element, B is at least a second element and O is an oxygen anion, and A, B, and O are not combined in a definite proportion. In an embodiment, the non-stoichiometric oxide has an elemental composition $A_xB_yO_{3-\delta}$, where A is at least the first element, B is at least the second element, O is the oxygen anion, and $\delta$ can be a positive or negative value with an absolute value greater than 0.001, preferably greater than 0.01.

In a particular embodiment, the electronically conducting perovskite-based oxide has an electronic conductivity of at least $10^{-1}$ S/cm at the gas stream temperature, and the electronically conducting perovskite-based oxide comprises a base oxide and a dopant, where the base oxide is one of $SrTiO_3$, $SrFeO_3$, $SrCoO_3$, $SrRuO_3$, $SrVO_3$, $LaMnO_3$, $LaCoO_3$, $LaCrO_3$, $LaFeO_3$, $LaCoO_3$, and where the dopant is at least one of Al, In, Sn, Zn, Ti, Ce, Sc, Ga, Nb, Sb, Ta, Ni, Co, Fe, Mn, Cr, Si, P, F, and Bf. In another embodiment, the base oxide and the dopant has an electronic carrier concentration of at least $10^{17}/cm^3$.

In an embodiment, the electronically conducting perovskite-based oxide has an electronic conductivity of at least $10^{-1}$ S/cm, where parameters are specified at the gas stream temperature following an elevated temperature reducing treatment. Here, "elevated temperature reducing treatment" means a treatment whereby the electronically conducting perovskite-based oxide material is contacted with a gaseous mixture having a composition of 4 vol. % $H_2$/balance $N_2$, where the gaseous mixture is at a temperature of at least 100° C., and where the contact occurs for a period of at least one hour. Such elevated reducing temperature treatments are generally effective for n-type electronically conducting perovskite-based oxides. Alternatively, in an embodiment, the electronically conducting perovskite-based oxide is a p-type electronically conducting perovskite-based oxide, and the parameters are specified at the gas stream temperature following an elevated temperature oxidizing treatment. Here, "elevated temperature oxidizing treatment" means a treatment whereby the conducting oxide material is contacted with a gaseous mixture having a composition of 20 vol. % $O_2$/balance $N_2$, where the gaseous mixture is at a temperature of at least 100° C., and where the contact occurs for a period of at least one hour. The respective elevated temperature treatments may occur during the fabrication of the electronically conducting perovskite-based oxide material or as a post-fabrication annealing process. In these embodiments, the phrases "following an elevated temperature reducing treatment" and "following an elevated temperature oxidizing treatment" is not intended to imply that the specific temperature treatments themselves are required as a limitation within the method of this disclosure. Rather, the phrases are utilized herein merely as a specific means by which the electronically conducting perovskite-based oxide materials of this disclosure may be identified.

The electronically conducting perovskite-based oxide material may be utilized for sensing the change in the chemical composition of the gas stream based on the impact of the chemical composition on the concentration and mobility of electronic charge carriers and defects that are also responsible for the relatively high electronic conductivity. Changes to the concentration and mobility of electronic charge carriers and defects directly impact the optical properties of the electronically conducting perovskite-based oxide material, which may be ascertained by monitoring optical transmission, reflection, scattering, and absorption spectra of the electronically conducting perovskite-based oxide material as ambient gas atmospheres are altered.

A fundamental origin of limitations of some metal oxides utilized for optical gas sensing applications arises from a calculated electronic band structure demonstrating a clear band-gap (Eg) between the conduction and valence bands, without the presence of significant defect levels or overlap in the vicinity of the Fermi level (Energy=0 eV). As a result of the electronic band structure, the optical absorbance of some metal oxides is relatively small and negligible in most practical cases for wavelengths greater than the wavelength corresponding to the energy associated with promotion of electrons from the valence to the conduction bands, i.e. the band gap (Eg). In contrast, in some embodiments of the electronically conducting perovskite-based oxides disclosed here, a unique electronic bandstructure responsible for the high electronic conductivity also results in an associated large broad-band optical absorption across the ultraviolet, visible, and near-infrared wavelength range. For these inherently electronically conducting perovskites often referred to as highly correlated systems, the unique electronic bandstructure responsible for the high electronic conductivity also results in contributions to the optical absorption spectrum that depend directly upon the oxidation state of the various cation elements. Such highly correlated perovskites generally fail to display a well-defined band gap. See e.g. Apgar et al., *Advanced Materials* 25 (2013), among others. Correspondingly, in certain embodiments, the electronically conducting perovskite-based oxide material is comprised of an electronically conducting perovskite-based oxide having a band gap less than 1 eV. Such low or poorly defined band gap perovskites can be advantageous for the enablement of broadband optical absorptions.

Figure 9:
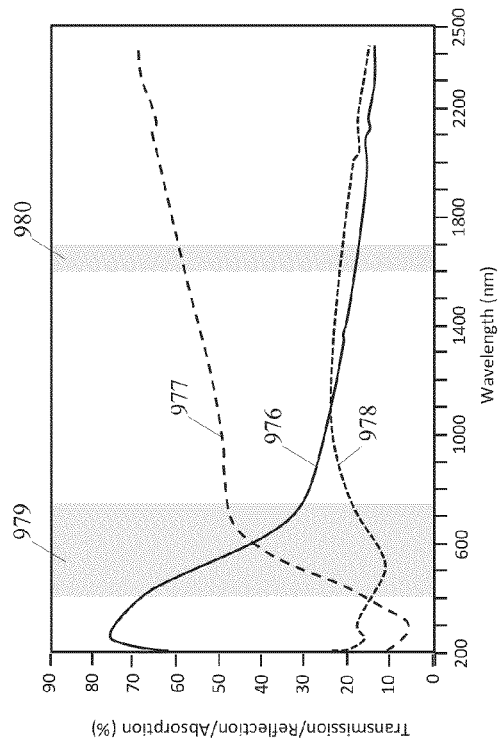
FIG. 9 illustrates measured optical spectra for an LSCF electronically conducting perovskite-based oxide film showing a broadband absorption over the UV, visible, near-infrared wavelength ranges.
Figure 8:
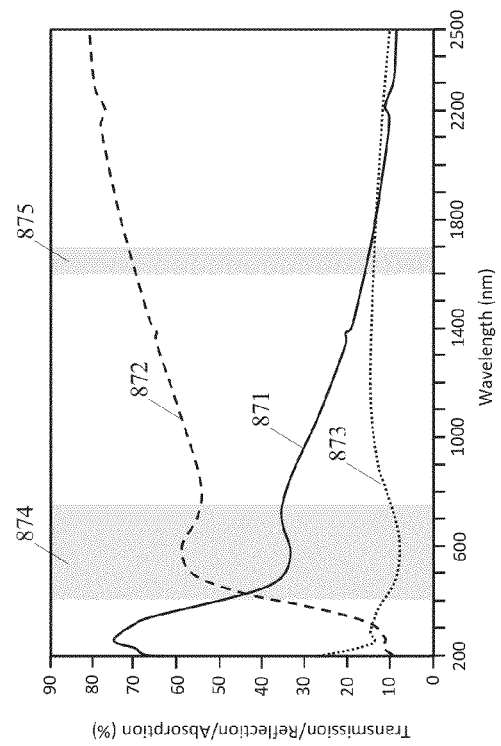
FIG. 8 illustrates measured optical spectra for an LSM electronically conducting perovskite-based oxide film showing a broadband absorption over the UV, visible, near-infrared wavelength ranges.

The broadband optical absorption exhibited by exemplary electronically conducting perovskite-based oxide films is illustrated at FIG. 8 for a $La_{1-x}Sr_xMnO_3$ (LSM) and FIG. 9 for a $La_{1-x}Sr_xCo_{1-y}Fe_yO_3$ (LSCF) films. At FIG. 8, transmission spectra 872, reflection spectra 873, and absorption spectra 871 are illustrated for the LSM, while at FIG. 9, transmission spectra 977, reflection spectra 978, and absorption spectra 976 are illustrated for the LSCF. The highlighted regions of the measured spectra indicate wavelength ranges for which a wide array of commercially available optical sources, detectors, and components can be readily acquired. In the visible range, nominally ~400-750 nm and indicated at 874 and 979, a wide array of light emitting diodes, lasers, and spectrometers are readily available. In the near-infrared range typically employed for telecommunications applications, nominally ~1500 nm-1600 nm and indicated at 875 and 980, a number of sophisticated tools for optical sensor fabrication and interrogation exist and can be leveraged in advanced sensor design. As such, the relatively broadband optical absorption of the electronically conductive perovskite-based oxides enables sensor devices to be designed with enhanced functionality and/or reduced overall cost and complexity by leveraging previously developed technologies, techniques, and optical components utilized in other major industries.

Figure 10:
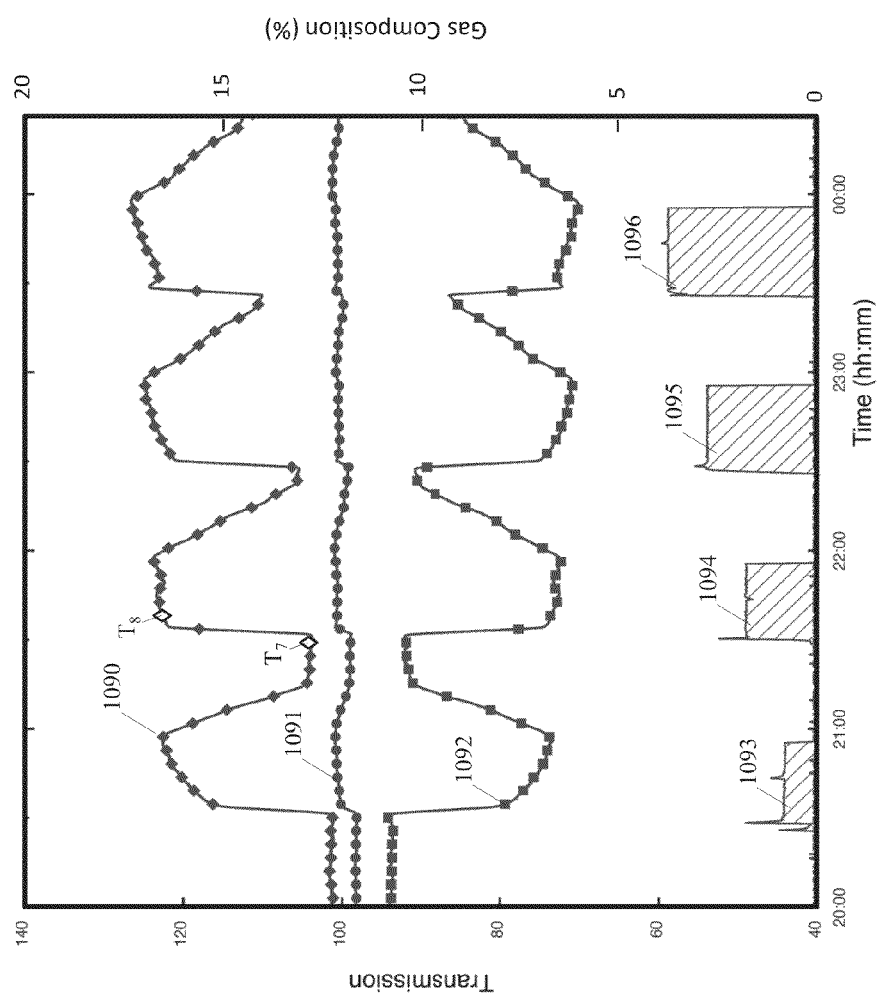
FIG. 10 illustrates a change in the optical transmission of an LSCF electronically conducting perovskite-based oxide in response to changes to a first chemical composition in the near-infrared wavelength range.
Figure 11:
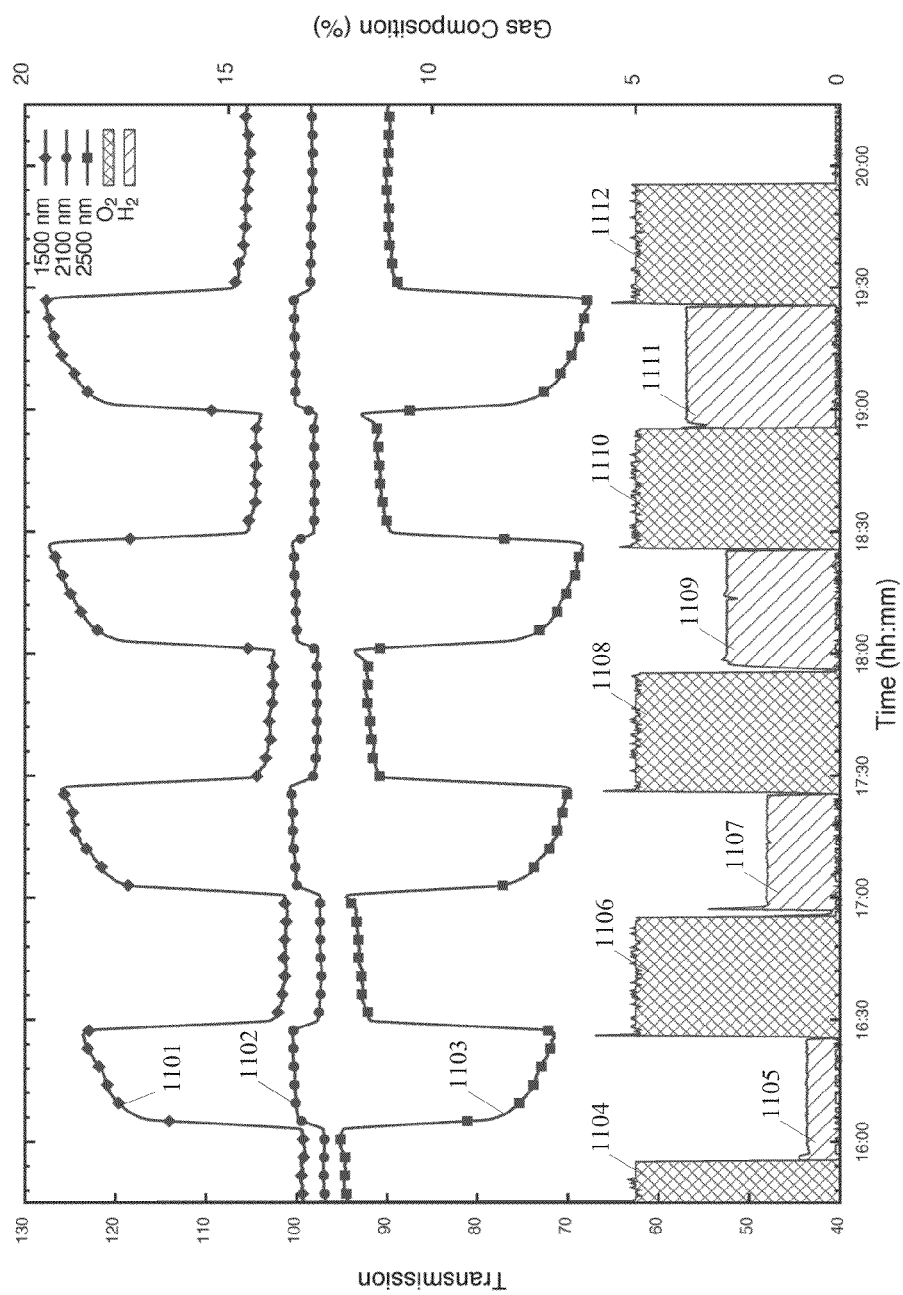
FIG. 11 illustrates a change in the optical transmission of an LSCF electronically conducting perovskite-based oxide in response to changes to a second chemical composition in the near-infrared wavelength range.

As an additional example, FIG. 10 represents exemplary optical signals expected for an electronically conductive perovskite-based oxide material comprising $La_{1-x}Sr_xCo_{1-y}Fe_yO_3$ when the $La_{1-x}Sr_xCo_{1-y}Fe_yO_3$ electronically conductive perovskite-based oxide material is illuminated by incident light and exposed to a monitored stream at a gas stream temperature of approximately 700° C. At FIG. 10, the particular optical signals represent the film transmission at several selected wavelengths, where 1090 illustrates the optical signal at a wavelength of about 1500 nm, 1091 illustrates the optical signal at a wavelength of about 2100 nm, and 1092 illustrates the optical signal at a wavelength of about 2500 nm. The chemical composition of the monitored stream is N2 with varying levels of $H_2$, where the % $H_2$ is illustrated at 1093, 1094, 1095, and 1096 and indicates % $H_2$ according to the Gas Composition (%) axis. Similarly, FIG. 11 represents exemplary optical signals expected for the $La_{1-x}Sr_xCo_{1-y}Fe_yO_3$ when $O_2$ is included in the recovery atmosphere between exposures to $H_2$. At FIG. 11, 1101 illustrates the optical signal at a wavelength of about 1500 nm, 1102 illustrates the optical signal at a wavelength of about 2100 nm, and 1103 illustrates the optical signal at a wavelength of about 2500 nm. Varying levels of $H_2$ with $N_2$ is illustrated at 1105, 1107, 1109, and 1111 with % $H_2$ according to the Gas Composition (%) axis. Additionally, the recovery atmosphere of about 5% $O_2$ with $N_2$ background is illustrated at 1104, 1106, 1108, 1110, and 1112. Comparison of FIGS. 10 and 11 illustrates that the presence of $O_2$ in the recovery atmosphere between exposures to $H_2$ results in significantly improved recovery times in some cases. Between the wavelength range of ~2000-2400 nm, a region of relative insensitivity of the optical signal to the changing composition of the gas stream also presents a potential opportunity for multi-parameter monitoring through broadband or multi-wavelength interrogation.

The electronically conductive perovskite-based oxide materials disclosed additionally display time constants advantageous for a gas sensing device, where here the time constant r represents the time it takes an optical signal's step response to reach about 63.2% of a final (asymptotic) value. For example, at FIG. 10, the time constant τ might be the time it takes optical signal 1090 to shift from $T_7$ to about 63.2% of a final value around $T_8$, when the step input represented by 1094 is supplied. In a particular embodiment, the time constant τ of the shift in the optical signal generated by the methodology disclosed is less than 15 minutes.

Figure 12:
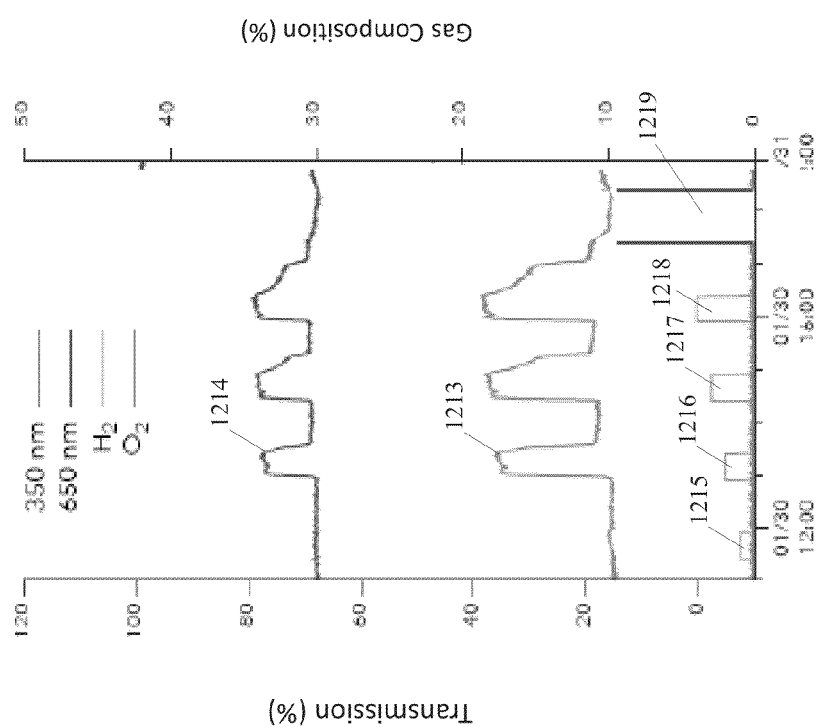
FIG. 12 illustrates a change in the optical transmission of an LSM20 electronically conducting perovskite-based oxide in response to changes to a chemical composition at a first and second interrogation wavelength.

As a further example, at FIG. 12, two different sets of optical signal shifts for a $La_{0.8}Sr_{0.2}MnO_3$ electronically conductive perovskite-based oxide material at a gas stream temperature of 500° C. are presented, where 1213 illustrates the optical signal at a wavelength of 350 nm and 1214 illustrates the optical signal at a wavelength of 650 nm Varying levels of $H_2$ with $N_2$ are illustrated at 1215, 1216, 1217, and 1218 with % $H_2$ according to the Gas Composition (%) axis. A 20% $O_2$/background $N_2$ gas stream was applied over the time period generally denoted by 1219. At both wavelengths, an optical signal shift in the positive direction is observed with the relative response being as large as 100% for the 350 nm optical signal for gas streams with greater than 2% $H_2$ in a background of $N_2$ as compared to the $H_2$-free gas streams consisting of $N_2$ or 20% $O_2$ balance $N_2$. In combination with the results illustrated at FIGS. 3 and 4, these additional results demonstrate the broadband nature of the measured optical responses of electronically conductive perovskite-based oxide materials. The broadband optical signal shift response to varying chemical composition of a gas stream improves compatibility with a wide range of available sources, detectors, and components for increased functionality or reduced cost of optical sensor devices that employ electronically conductive perovskite-based oxide materials.

Figure 13:
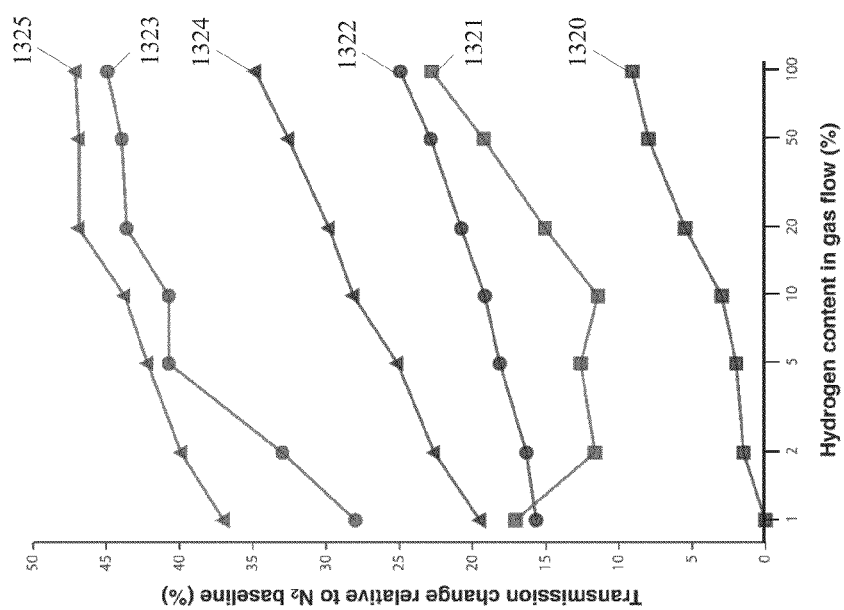
FIG. 13 illustrates a change in the optical transmission of an optical fiber sensor coated with electronically conducting perovskite-based oxides showing an increased response at high temperatures associated with an increased electronic conductivity.

FIG. 13 illustrates the increased response with generally occurs as a result of doping, as well as increased responses which may occur as temperatures increase. FIG. 13 illustrates transmission changes for various $H_2$ concentrations relative to the transmission experienced for a substantially 100% $N_2$ baseline, depicted for both $SrTiO_3$ and $La_{0.3}Sr_{0.7}TiO_3$ at temperatures of 600° C., 700° C., and 800° C. At FIG. 13, 1320 represents the relative transmission of $SrTiO_3$ while 1321 represents the relative transmission of $La_{0.3}Sr_{0.7}TiO_3$ at a temperature of 600° C. for the various $H_2$ concentrations; 1322 represents the relative transmission of $SrTiO_3$ while 1323 represents the relative transmission of $La_{0.3}Sr_{0.7}TiO_3$ at a temperature of 700° C. for the various $H_2$ concentrations, and; 1324 represents the relative transmission of $SrTiO_3$ while 1325 represents the relative transmission of $La_{0.3}Sr_{0.7}TiO_3$ at a temperature of 800° C. for the various $H_2$ concentrations. As can be observed, generally the response is increased with higher temperatures and higher doping concentrations for these La-doped $SrTiO_3$ materials which are also related to an enhanced electronic conductivity. It is also observed that in most cases, the change in transmission with increasing hydrogen content in the gas flow is monotonic over the entire range from 0-100% by volume.

Figure 14:
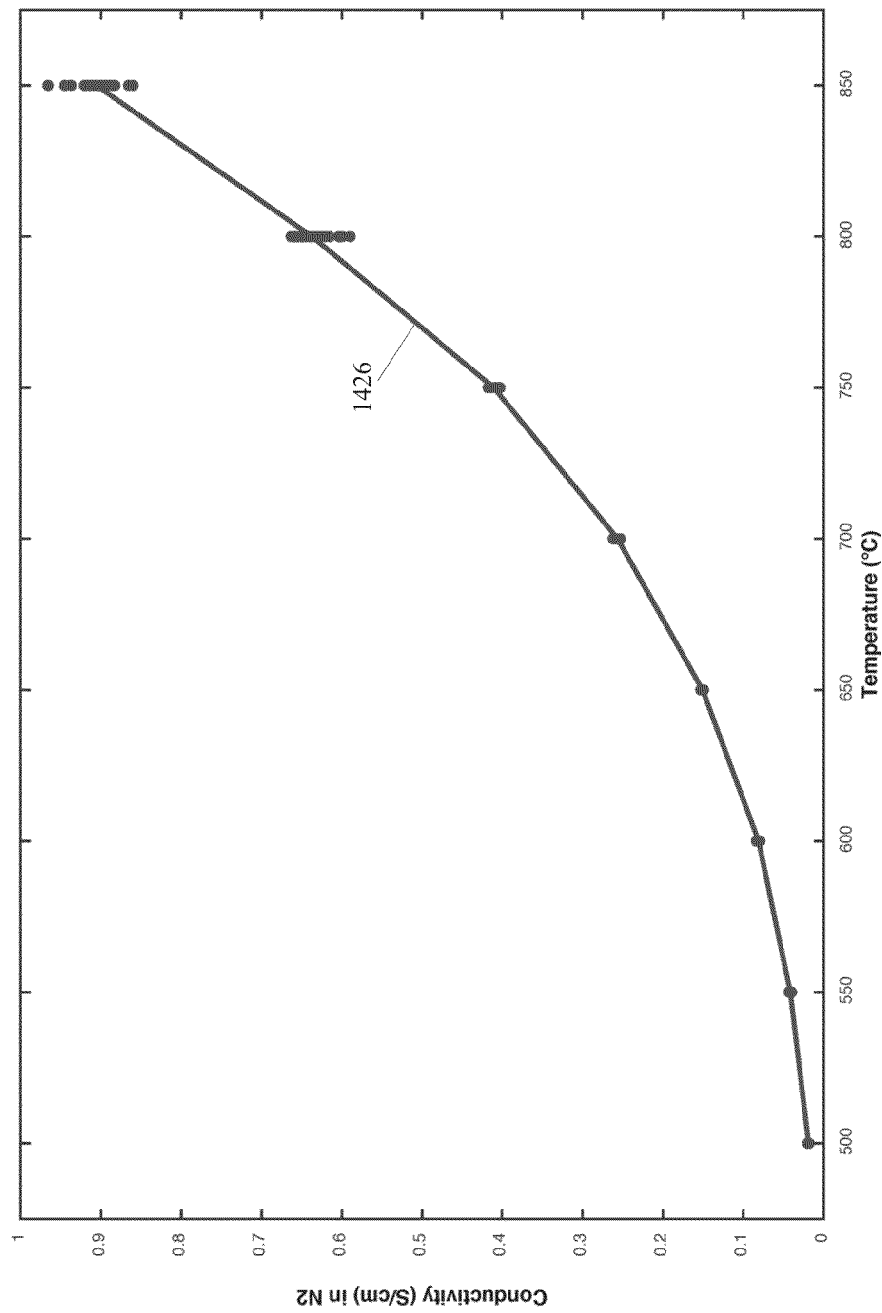
FIG. 14 illustrates the impact of gas stream temperature on the electrical conductivity.

As discussed, the conductivity of the electrically conductive perovskite-based oxide is at least $10^{-1}$ S/cm at the gas stream temperature. As is understood, electrical conductivities may be expected to increase with temperature for at least some of the conductive perovskite-based oxides disclosed here. For example, FIG. 14 illustrates the increase in electrical conductivity 1426 for the electrically conductive perovskite-based oxide $SrTiO_3$ in a gas stream of $N_2$ as temperatures increase from about 500° C. to about 850° C. As a result of this relationship between electrical conductivity and temperature, in some embodiments the gas stream has a temperature of at least 200° C.

As discussed, the electronically conductive perovskite-based oxide materials disclosed provide for relatively large signal shifts. In an embodiment, the change in the chemical composition of the monitored stream is indicated by an increase or decrease in a signal-averaged optical signal of at least 0.1%, preferably at least 0.5%, more preferably at least 1%, and still more preferably at least 5%. Here, the signal-averaged optical signal is generated through a signal processing technique applied in the time domain, and the increase or decrease of 0.1% means that an observed signal-averaged optical signal is at least 0.1% greater or lesser than an initial signal-averaged optical signal. For example, an increase or decrease of 0.1% in an observed signal-averaged optical signal when the signal-averaged optical signal is a transmittance or absorptance characterized as $\tau_\lambda=I/I_o$ or $A_\lambda=(I_o-I)/I_o$ respectively, where $I_o$ is the intensity of the incident light and where I is the intensity of the exiting light at a wavelength $\lambda$, and where intensity refers to a power transmitted per unit area. In an embodiment, the signal-averaged optical signal is a time-averaged optical signal based on an absorption, transmission, scattering, or reflection generated using the conducting oxide material and averaged over some time interval $\Delta t$. Techniques for the generation of signal-averaged optical signals are known in the art. See e.g. R. Lyons, *Understanding Digital Signal Processing* ($3^{rd}$ Ed., 2010); and see R. Northrup, *Analysis and Application of Analog Electronic Circuits to Biomedical Instrumentation* (2005), among others.

The electronically conducting perovskite based oxide may comprise the electronically conducting perovskite based oxide material in conjunction with a combination of other materials, however the primary response observed, monitored, and discussed herein is the response of the electronically conducting perovskite based oxide to the change in the chemical composition of the monitored stream. In an embodiment, the electronically conducting perovskite based oxide material is a mixture of compounds, and the electronically conducting perovskite based oxide comprises at least 25 wt. % and preferably 50 wt. % of the electronically conducting perovskite based oxide material. In another embodiment, the electronically conducting perovskite based oxide material is characterized by less than 1 wt. %, less than 0.1 wt. %, or undetectable noble metal deposits. Here a "noble metal deposit" means a deposit in contact with the electronically conducting perovskite based oxide material where one or more noble metals comprise at least 90 wt. % of the noble metal deposit, and where the noble metal deposit is not a cation or anion of the $A_xB_yO_{3-\delta}$, electronically conducting perovskite based oxide and are not located at a special position of the $A_xB_yO_{3-\delta}$, lattice structure. Noble metals within this context include gold, silver, platinum, palladium, ruthenium, rhodium, osmium, and iridium. In a further embodiment, the conducting oxide material comprises less than 1 wt. %, less than 0.1 wt. %, or undetectable gold, silver, or palladium.

Without being bound by theory, the optical response of the electronically conducting perovskite based oxide materials achieved within this disclosure is believed to result from the high electronic conductivity of the metal oxide comprising the electronically conducting perovskite based oxide material, and a resulting impact of changing gas atmospheres on the concentration and mobility of electronic charge carriers and defects responsible for the relatively high electronic conductivity. It is known that certain metal oxides such as $TiO_2$, ZnO, and $SnO_2$ exhibit changes in electrical resistance as a function of temperature and/or in response to changing gas atmospheres, which is usually associated with a change in the free carrier density and mobility of the oxide. Additionally, for electronically conducting perovskite based oxides such as $La_{1-x}Sr_xMnO_3$, $La_{1-x}Sr_xCoO_3$, and $La_{1-x}Sr_xCo_{1-y}Fe_yO_3$, a dependence of electrical resistance, defect concentration, and carrier concentration and mobility on ambient atmospheric conditions at high temperatures is also expected. See e.g. Petrov et al. "Oxygen Nonstoichiometry of $La_{1-x}Sr_xCoO_{3-d}$ (0<x≤0.6)" *Journal of Solid State Chemistry* 87 (1990); see also Lankhorst et al., "Thermodynamic Quantities and Defect Structure of $La_{0.6}Sr_{0.4}Co_{1-y}Fe_yO_{3-d}$ (y=0-0.6) from High-Temperature Coulometric Titration Experiments", *Journal of Solid State Chemistry* 130 (1997). Within this disclosure, these changes in effective densities of defects and densities and mobilities of electronic charge carriers of electronically conducting perovskite based oxides in response to changing ambient gas atmospheres are postulated to be responsible for the change in measured optical signals (transmission, absorption, reflection). This surprising discovery is utilized within this disclosure to provide a means whereby electronically conducting perovskite based oxides having relatively high electronic conductivity can be employed to generate useful signals indicating alterations in a surrounding gas atmosphere, based on resulting shifts in the optical signal.

In an embodiment, the change in the chemical composition of the monitored stream is an increased concentration of a reducing gas. Here, "reducing gas" means a gaseous constituent that alters the defect and electronic charge carrier concentration and mobility of the electronically conducting perovskite based oxide comprising the electronically conducting perovskite based oxide material as a result of contact between the gaseous constituent and the electronically conducting perovskite based oxide. For example, when the electronically conducting perovskite based oxide is an n-type oxide, the reducing gas might be expected to increase the electronic conductivity and electronic charge carrier concentration. Exemplary reducing gases include $H_2$, CO, ammonia ($_NH_3$), and hydrocarbons (e.g. fuel gases such as methane, ethane), among others. In another embodiment, the change in the chemical composition of the monitored stream is an increased concentration of an oxidizing gas, where "oxidizing gas" means a gaseous constituent altering the electronic conductivity and carrier concentration of the electronically conducting perovskite based oxide comprising the electronically conducting perovskite based oxide material as a result of contact between the gaseous constituent and the metal oxide. For example, when the electronically conducting perovskite based oxide is an n-type oxide, the oxidizing gas might be expected to decrease the electronic conductivity and the electronic charge carrier concentration. Exemplary oxidizing gases include $O_2$, $O_3$, NOx, SOx, halogens (e.g. $F_2$, $_Cl_2$, $_Br_2$, and $I_2$), halogen compounds, sulfuric acids ($H_2SO_4$, $H_2S_2O_8$, and $H_2SO_5$), nitric acid and nitrate compounds, among others. The impact of a reducing or oxidizing gas on the electronic conductivity, electronic charge carrier concentration and mobility of the electronically conducting perovskite based oxide may be determined by any means known in the art, such as Hall effect measurement. See e.g., Ramsden, Edward, *Hall Effect Sensors: Theory and Application*, (2nd Ed., 2006), among others.

The electronically conducting perovskite based oxide material may be in the form of dispersed nanoparticles, an aggregate nanoparticle film, or a largely dense and continuous film. When the electronically conducting perovskite based oxide material is in the form of dispersed nanoparticles or an aggregate nanoparticle film, this means that a plurality of particles comprise the electronically conducting perovskite based oxide material, and that some portion of the electronically conducting perovskite based oxide comprising the electronically conducting perovskite based oxide material comprises each particle in the plurality. In an embodiment, the plurality of nanoparticles has a Sauter mean diameter of less than 100 micron. The Sauter mean diameter may be determined by means known in the art. See e.g., Rhodes, Martin, *Introduction to Particle Technology* ($2^{nd}$ ed. 2008). Additionally, when the electronically conducting perovskite based oxide material is in the form of dispersed nanoparticles, this means that the plurality of nanoparticles are sufficiently separated such that the plurality of nanoparticles displays an electrical conductance of less than $\frac{1}{10}$th of the electrical conductance of the metal oxide comprising the electronically conducting perovskite based oxide material. Such a condition can be determined using various methods for the evaluation of proximity to a percolation limit in supported nanoparticle systems. See e.g. Trudeau et al., "Competitive transport and percolation in disordered arrays of molecularly linked Au nanoparticles," *J. Chem. Phys., Vol.* 117 (2002), among others. Further, when the electronically conducting perovskite based oxide material is in the form of an aggregate nanoparticle film, this means the plurality of nanoparticles displays an electrical conductance of at least $\frac{1}{10}$th of the electrical conductance of the metal oxide comprising the electronically conducting perovskite based oxide material, and that a given volume containing the plurality of nanoparticles has a void fraction of at least 20%. Void fraction may be determined using means known in the art. See e.g., Yancey et al., "The influence of void space on antireflection coatings of silica nanoparticle self assembled films," *J. Appl. Phys.* 99 (2006), and associated references. When the electronically conducting perovskite based oxide material is in the form of a continuous film, this means that a given volume containing the electronically conducting perovskite based oxide material has a void fraction of less than 20%. Additionally, it is understood that the nanoparticles of this disclosure are not limited to strictly spherical shapes, and that a plurality of nanoparticles may take shapes such as triangular prisms, disks, shells, wires, rods, and others.

The electronically conducting perovskite based oxide material utilized in the method of this disclosure may be prepared using means known in the art for the production of dispersed nanoparticles, aggregate nanoparticle film, or a continuous film as disclosed herein. See e.g. Ohodnicki et al., "Plasmonic Transparent Conducting Metal Oxide Nanoparticles and Nanoparticle Films for Optical Sensing Applications," *Thin Solid Films* (2013), doi: 10.1016/j.tsf.2013.04.145, among others.

At FIGS. 1 and 2, the monitored stream G is some portion of a gas stream. In an embodiment, the gas stream and the monitored stream are separated by a barrier layer, such as a dense filter layer to act as a diffusion barrier or a sieve material having an average pore size that is tailored to improve selectivity. Such an arrangement may be helpful when the gas stream is comprised of a molecular constituent which may need to be excluded from influencing the sensing operation. For example, a sieve material may be utilized to exclude the molecular constituent from the monitored stream by selecting a sieve material having an average pore size less than the molecular diameter of the molecular constituent to be excluded. Exemplary sieves include aluminosilicate minerals, clays, porous glasses, microporous charcoals, zeolites, active carbons, or synthetic compounds which display a standardized average pore size, such as pore size 3A, pore size 4A, etc. In a similar manner, the dense filter layer can be selected such that the diffusion of a species to be excluded is relatively sluggish. For example, exemplary filters might include films comprised of $SnO_2$, $SiO_2$, Palladium alloys, and others materials known for the selective filtering of hydrogen in an operation where the conducting oxide material is utilized to detect changes in an $H_2$ concentration. An appropriately defined barrier layer can also protect the underlying gas oxide sensing material from the presence of particulates and undesirable corrosive species that may have a deleterious effect on long term stability of the gas oxide sensing material. In an embodiment, a first surface of the barrier material is contacted with the gas stream, and the monitored stream is withdrawn from a second surface of the barrier material.

Figure 16:
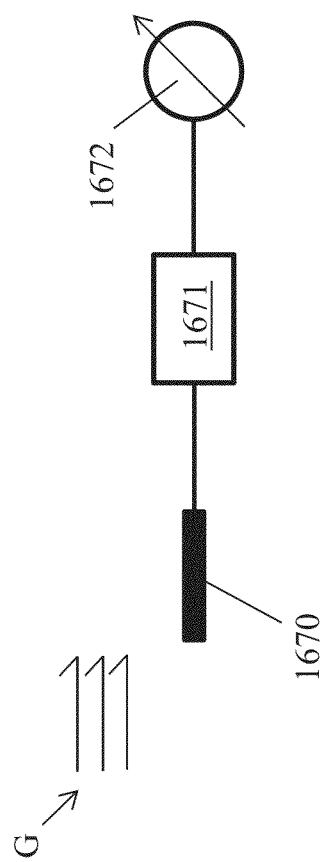
FIG. 16 illustrates an instrument utilizing the electronically conducting perovskite-based oxide material.

In another embodiment, the monotonic response of the electronically conducting perovskite based oxide material displayed in response to increasing or decreasing concentrations of chemical species is utilized in a method of determining the concentration of a chemical species in a monitored stream. In this embodiment, the electronically conducting perovskite based oxide material comprises a sensing head in a sensing instrument, where the sensing head communicates with an interrogator and a metered response is provided. The methodology is represented at FIG. 16, where the electronically conducting perovskite based oxide material of this disclosure comprises sensing head 1670 in contact with monitored stream G. Monitored stream G is comprised of a chemical composition of gaseous constituents with concentrations varying over time. Interrogator 1671 illuminates the electronically conducting perovskite based oxide comprising sensing head 1670 with incident light and gathers exiting light. Interrogator 1671 compares the incident light and the exiting light and generates a measurand, where the measurand is proportional to a shift in the optical signal as defined herein. Such interrogators for use in optical systems are known the art. See e.g., Lee et al., "Review of the present status of optical fiber sensors," *Optical Fiber Technology* 9 (2003), and associated references. Interrogator 1671 is in data communication with meter 1672 which provides an indication of the magnitude of the measurand generated and communicated by interrogator 1671. The monotonic response of the electronically conducting perovskite based oxide material to increasing or decreasing concentrations of a chemical species in monitored stream G allows the measurand generated by interrogator 1671 and interpreted for display by meter 1672 to provide an indication of the concentration of the chemical species present. In this embodiment, the steps of illuminating the gas sensing oxide material, collecting exiting light, and monitoring an optical signal based on a comparison of the incident light and the exiting light is conducted by interrogator 1671, and detecting a shift in the optical signal is conducted through observation of meter 1672. An indication of the concentration of the chemical species present in monitored stream G is provided by comparison of the observed meter reading and a reference meter reading, where the reference meter reading results from a reference measurand generated under reference conditions, for example when monitored stream G consists solely of the background $N_2$, or some other condition.

Figure 17:
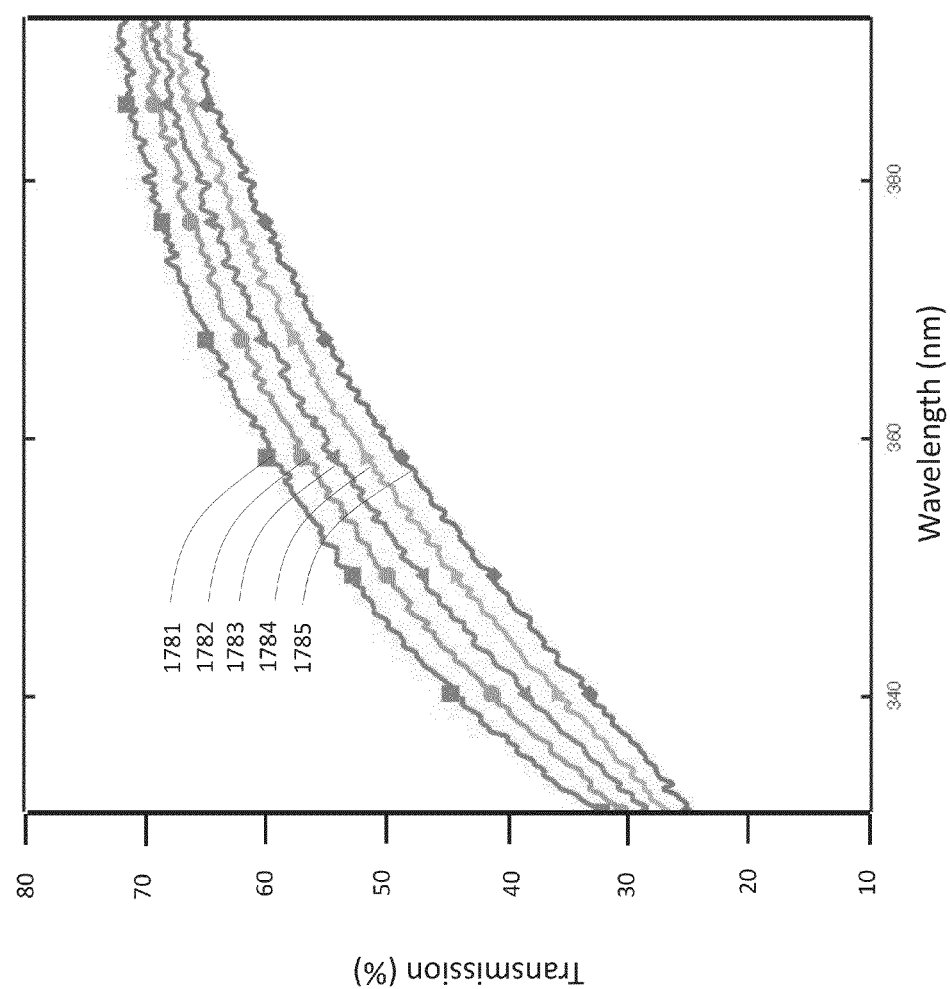
FIG. 17 illustrates a shift in the optical signal edge with increasing temperatures.

FIG. 17 illustrates the impact of temperature on the optical signal edge of a $SrTiO_3$ electronically conducting perovskite based oxide over wavelengths from about 330 nm to about 390 nm, where 1781 indicates transmission at 20° C., 1782 indicates transmission at 200° C., 1783 indicates transmission at 400° C., 1784 indicates transmission at 600° C., and 1785 indicates transmission at 800° C. Such behavior as illustrated at FIG. 17 allows for the possibility of utilizing the electronically conducting perovskite based oxides disclosed for temperature measurement in addition to chemical sensing, including simultaneous measurement of temperature and chemical sensing using optical means which may involve broadband or multi-wavelength interrogation approaches.

Thus, provided here is a method for detecting a change in the chemical composition of monitored stream which utilizes changes in the optical signal generated by an electronically conducting perovskite based oxide material. The electronically conducting perovskite based oxide material comprises a metal oxide having a perovskite-based crystal structure and an electronic conductivity of at least $10^{-1}$ S/cm, at the gas stream temperature. In an embodiment, the metal oxide is an electronically conducting perovskite based oxide and A comprises at least a first element and a second element, B comprises a third element, and both A and B are bonded with the oxygen anion. Exemplary electronically conducting perovskite-based oxides include but are not limited to $La_{1-x}Sr_xCoO_3$, $La_{1-x}Sr_xMnO_3$, $LaCrO_3$, $LaNiO_3$, $La_{1-x}Sr_xMn_{1-y}Cr_yO_3$, $SrFeO_3$, $SrVO_3$, La-doped $SrTiO_3$, Nb-doped $SrTiO_3$, and $SrTiO_{3-\delta}$. Changes in the chemical composition of a monitored stream in contact with the electronically conducting perovskite based oxide material are detected based on a shift in the optical signal generated through comparison of incident and exiting light using optical spectroscopy. In a specific embodiment, the electronically conducting perovskite based oxide material is illuminated by light propagating along a waveguide, such as a fiber optic core material. The method is particularly useful for monitoring the chemical composition of gaseous streams at elevated temperatures.

It is to be understood that the above-described arrangements are only illustrative of the application of the principles of the present invention and it is not intended to be exhaustive or limit the invention to the precise form disclosed. Numerous modifications and alternative arrangements may be devised by those skilled in the art in light of the above teachings without departing from the spirit and scope of the present invention. It is intended that the scope of the invention be defined by the claims appended hereto.

In addition, the previously described versions of the present invention have many advantages, including but not limited to those described above. However, the invention does not require that all advantages and aspects be incorporated into every embodiment of the present invention.

All publications and patent documents cited in this application are incorporated by reference in their entirety for all purposes to the same extent as if each individual publication or patent document were so individually denoted.

What is claimed is:

1. A method of a detecting a change in a chemical composition of a gas stream comprising:
    contacting an electronically conducting perovskite based oxide material with some portion of the gas stream, where the some portion of the gas stream has a gas stream temperature, and where the electronically conducting perovskite based oxide material comprises a electronically conducting perovskite based oxide, where the electronically conducting perovskite based oxide has an electronic conductivity of at least $10^{-1}$ S/cm at the gas stream temperature;
    illuminating the electronically conducting perovskite based oxide material with a light source emitting incident light;
    collecting exiting light, where the exiting light is light that originates at the light source and is transmitted, reflected, scattered or a combination thereof by the electronically conducting perovskite based oxide;
    monitoring an optical signal based on a comparison of the incident light and the exiting light using optical spectroscopy; and
    detecting a shift in the optical signal, thereby detecting the change in the chemical composition, and thereby monitoring the chemical composition of the gas stream.

2. The method of claim 1 where the electronically conducting perovskite based oxide has a perovskite based crystal structure having an A-site and a B-site and having an empirical formula $A_xB_yO_{3-\delta}$, where A is at least a first element at the A-site of the perovskite based crystal structure, B is at least a second element at the B-site of the perovskite based crystal structure, and O is an oxygen anion coordinated to both A and B, and where $0.8<x<1.2$, $0.8<y<1.2$, and $\delta$ is a number having an absolute value greater than or equal to zero.

3. The method of claim 2 where A comprises an element A' and a second element A" and where B comprises an element B' and a second element B", and where the electronically conducting perovskite based oxide has an empirical formula $A'_{(x-a)}A''_aB'_{(y-b)}B''_bO_{3-\delta}$, and where $0 \leq a$ and where $0 \leq b$.

4. The method of claim 3 where the second element A" and the second element B" are less than 15 wt. % of the electronically conducting perovskite based oxide.

5. The method of claim 3 where the electronically conducting perovskite based oxide has a bandgap of less than 1 eV.

6. The method of claim 3 where the electronically conducting perovskite based oxide comprises $La_{1-x}Sr_xCoO_3$, $La_{1-x}Sr_xMnO_3$, $La_{1-x}Sr_xMn_{1-y}Cr_yO_3$, La-doped $SrTiO_3$, and Nb-doped $SrTiO_3$ or mixtures thereof.

7. The method of claim 3 where some portion of the gas stream has a temperature of at least 200° C.

8. The method of claim 7 where the optical signal is a signal-averaged optical signal, and where the shift in the optical signal is detected when an observed signal-averaged optical signal is at least 0.1% greater or lesser than an initial signal-averaged optical signal.

9. The method of claim 7 where the incident light and the exiting light comprise light at a wavelength between 250 and 400 nanometers, and where the optical signal is based on the comparison of the incident light and the exiting light at the wavelength between 250 and 400 nanometers.

10. The method of claim 7 where the incident light and the exiting light comprise light at a wavelength between 1000 and 3750 nanometers, and where the optical signal is based on the comparison of the incident light and the exiting light at the wavelength between 1000 and 3750 nanometers.

11. The method of claim 7 where the incident light and the exiting light comprise light at a wavelength between 400 and 1000 nanometers, and where the optical signal is based on the comparison of the incident light and the exiting light at the wavelength between 400 and 1000 nanometers.

12. The method of claim 7 where the electronically conducting perovskite based oxide material has an rms surface roughness of at least 15 nanometers.

13. The method of claim 7 where the change in the chemical composition a change in the concentration of a reducing gas, where the reducing gas comprises $H_2$, CO, $NH_3$, a hydrocarbon, or mixtures thereof.

14. The method of claim 7 where the change in the chemical composition is a change in the concentration of an oxidizing gas, where the oxidizing gas comprises $O_2$, $O_3$, NOx, SOx, a halogen, a halogen compound, a sulfuric acid, a nitric acid, a nitrate, or mixtures thereof.

15. The method of claim 3 where the gas stream is comprised of a molecular gas constituent, and further comprising:
utilizing a barrier layer, where the barrier layer material has a first surface and a second surface, where the first surface and the second surface are separated by at least some portion of the barrier layer; and
contacting the first surface of the barrier layer and the gas stream, and withdrawing the some portion of the gas stream from the second surface of the barrier layer, thereby contacting the electronically conducting perovskite-based material with the some portion of the gas stream.

16. The method of claim 3 further comprising:
providing a waveguide comprised of a core material;
placing the electronically conducting perovskite-based oxide material in contact with the core material; and
emitting the incident light from the light source into the core material and illuminating the electronically conducting perovskite-based metal oxide, thereby illuminating the electronically conducting perovskite-based oxide with the light source emitting the incident light.

17. The method of claim 3 further comprising monitoring the chemical composition of the gas stream by measuring a resistance of the electronically conducting perovskite-based metal oxide.

18. A method of determining a concentration of a chemical species in the monitored stream using the method of claim 3, further comprising:
emitting incident light using an interrogator in optical communication with the electronically conducting perovskite-based metal oxide material and illuminating the electronically conducting perovskite-based metal oxide material, and gathering exiting light using the interrogator in optical communication with the electronically conducting perovskite-based metal oxide material, and generating the optical signal based using the interrogator, thereby illuminating the gas sensing oxide material with the light source emitting incident light, collecting exiting light, and monitoring the optical signal based on the comparison of the incident light and the exiting light using optical spectroscopy;
generating a measurand using the interrogator based on the optical signal and communicating the measurand to a meter in data communication with the interrogator;
receiving the measurand at the meter and displaying a meter reading on the meter based on the measurand, and observing the meter reading, thereby generating an observed meter reading;
evaluating a difference between the observed meter reading and a reference meter reading, thereby detecting a shift in the optical signal; and
assigning a value to the concentration of the chemical species based on the difference between the observed meter reading and the reference meter reading, thereby determining the concentration of the chemical species in the monitored stream.

19. A method of a detecting a change in a concentration of a reducing gas in a gas stream comprising:
generating the gas stream, where the gas stream comprises the reducing gas, and where the gas stream has a temperature of at least 200° C.;
contacting an electronically conducting perovskite-based metal oxide material with some portion of the gas stream, where some portion of the gas stream has a gas stream temperature, where the gas stream temperature is at least 200° C., and where the electronically conducting perovskite-based metal oxide material comprises an electronically conducting perovskite-based metal oxide, where the electronically conducting perovskite-based metal oxide has a perovskite based crystal structure having an A-site and a B-site and having an empirical formula $A_xB_yO_{3-\delta}$, where A is at least a first element at the A-site of the perovskite based crystal structure, B is at least a second element at the B-site of the perovskite based crystal structure, and O is an oxygen anion coordinated to both A and B, and where $0.8<x<1.2$, $0.8<y<1.2$, and $\delta$ is number that renders the composition charge neutral, and where the electronically conducting perovskite-based metal oxide has a perovskite-based crystal structure and an electronic conductivity of at least $10^2$ S/cm at the gas stream temperature;
illuminating electronically conducting perovskite-based metal oxide with a light source emitting incident light;
collecting exiting light, where the exiting light is light that originates at the light source and is transmitted, reflected, or a combination thereof by the electronically conducting perovskite-based metal oxide;
monitoring an optical signal based on a comparison of the incident light and the exiting light using optical spectroscopy; and
detecting a shift in the optical signal, thereby detecting the change in the concentration of the reducing gas in the gas stream.

20. The method of claim 19 where the electronically conducting perovskite-based metal oxide is a non-stoichiometric oxide.

* * * * *